(12) United States Patent
Peng et al.

(10) Patent No.: US 8,092,369 B2
(45) Date of Patent: *Jan. 10, 2012

(54) ORGAN MANIPULATOR HAVING SUCTION MEMBER SUPPORTED WITH FREEDOM TO MOVE RELATIVE TO ITS SUPPORT

(75) Inventors: Steven Peng, Burlingame, CA (US); Larry Voss, San Jose, CA (US); David E. Hancock, San Francisco, CA (US); Grace A. Carlson, San Francisco, CA (US); John W. Davis, Sunnyvale, CA (US); Albert K. Chin, Palo Alto, CA (US); Jaime S. Vargas, Palo Alto, CA (US)

(73) Assignee: MAQUET Cardiovascular LLC, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/837,391

(22) Filed: Jul. 15, 2010

(65) Prior Publication Data

US 2010/0280324 A1     Nov. 4, 2010

Related U.S. Application Data

(60) Continuation of application No. 11/789,383, filed on Apr. 23, 2007, now Pat. No. 7,766,817, which is a continuation of application No. 10/801,024, filed on Mar. 15, 2004, now Pat. No. 7,226,409, which is a continuation of application No. 09/747,388, filed on Dec. 22, 2000, now Pat. No. 6,730,020, which is a division of application No. 09/390,792, filed on Sep. 7, 1999, now Pat. No. 6,506,149.

(51) Int. Cl.
    A61F 13/00    (2006.01)
(52) U.S. Cl. .......................................................... 600/37
(58) Field of Classification Search ................... 600/37, 600/201–202, 206, 215, 219, 227–228, 231, 600/233, 235; 128/897–898; 601/132; 606/151; 248/276.1, 288.51, 316.4
See application file for complete search history.

(56) References Cited

U.S. PATENT DOCUMENTS 2,082,782 A    6/1937  Allen
(Continued)

FOREIGN PATENT DOCUMENTS

DE    3138589 A1    4/1983
(Continued)

OTHER PUBLICATIONS

Grundeman et al., "Vertical Displacement of the Beating Heart by the Octopus Tissue Stabilizer: Influence on Coronary Flow," Ann Thorac Surg. 1998;65:138-52.

(Continued)

Primary Examiner — John Lacyk
(74) Attorney, Agent, or Firm — Alan W. Cannon; Law Office of Alan W. Cannon

(57) ABSTRACT

An organ manipulator including at least one suction member or adhesive disk mounted to a joint providing freedom of movement of the at least one suction member or adhesive disk relative to its support. A method for retracting and maintaining an organ in a retracted position using suction (or adhesive force) so that the organ is free to move normally (e.g., to beat or undergo other limited-amplitude motion) is provided.

11 Claims, 14 Drawing Sheets

U.S. PATENT DOCUMENTS

| | | |
|---|---|---|
| 3,466,079 A | 9/1969 | Mammel |
| 3,584,822 A | 6/1971 | Oram |
| 3,912,317 A | 10/1975 | Ohnaka et al. |
| 3,916,909 A | 11/1975 | Kletschka et al. |
| 4,049,002 A | 9/1977 | Kletschka et al. |
| 4,049,484 A | 9/1977 | Priest et al. |
| 4,094,484 A | 6/1978 | Galione et al. |
| 4,096,853 A | 6/1978 | Weigand |
| 4,217,890 A | 8/1980 | Owens |
| 4,350,160 A | 9/1982 | Kolesov et al. |
| 4,457,300 A | 7/1984 | Budde |
| 4,637,377 A | 1/1987 | Loop |
| D293,470 S | 12/1987 | Adler |
| 4,827,926 A | 5/1989 | Carol |
| 4,852,552 A | 8/1989 | Chaux |
| 4,904,012 A | 2/1990 | Nishiguchi et al. |
| 4,949,927 A | 8/1990 | Madocks et al. |
| 4,957,477 A | 9/1990 | Lundback |
| 5,019,086 A | 5/1991 | Neward |
| 5,131,905 A | 7/1992 | Grooters |
| 5,139,517 A | 8/1992 | Corral |
| 5,150,706 A | 9/1992 | Cox et al. |
| 5,192,070 A | 3/1993 | Nagai et al. |
| 5,245,705 A | 9/1993 | Swaney et al. |
| 5,256,132 A | 10/1993 | Sayders |
| 5,290,082 A | 3/1994 | Palmer et al. |
| 5,348,259 A | 9/1994 | Blanco et al. |
| 5,417,709 A | 5/1995 | Slater |
| 5,452,733 A | 9/1995 | Sterman et al. |
| 5,453,078 A | 9/1995 | Valentine et al. |
| 5,480,425 A | 1/1996 | Ogilive |
| 5,484,391 A | 1/1996 | Buckman, Jr. et al. |
| 5,509,890 A | 4/1996 | Kazama |
| 5,536,251 A | 7/1996 | Evard et al. |
| 5,569,274 A | 10/1996 | Rapacki et al. |
| 5,571,215 A | 11/1996 | Sterman et al. |
| 5,613,937 A | 3/1997 | Garrison et al. |
| 5,632,746 A | 5/1997 | Middleman et al. |
| 5,662,300 A | 9/1997 | Michelson |
| 5,713,951 A | 2/1998 | Garrison et al. |
| 5,727,569 A | 3/1998 | Benetti et al. |
| 5,728,151 A | 3/1998 | Garrison et al. |
| 5,730,757 A | 3/1998 | Benetti et al. |
| 5,735,290 A | 4/1998 | Sterman et al. |
| 5,766,151 A | 6/1998 | Valley et al. |
| 5,782,746 A | 7/1998 | Wright |
| 5,797,960 A | 8/1998 | Stevens et al. |
| 5,799,661 A | 9/1998 | Boyd et al. |
| 5,807,243 A | 9/1998 | Vierra et al. |
| 5,836,311 A | 11/1998 | Borst et al. |
| 5,865,730 A | 2/1999 | Fox et al. |
| 5,885,271 A | 3/1999 | Hamilton et al. |
| 5,894,843 A | 4/1999 | Benetti et al. |
| 5,899,425 A | 5/1999 | Corey et al. |
| 5,906,607 A | 5/1999 | Taylor et al. |
| 5,927,284 A | 7/1999 | Borst et al. |
| 5,957,835 A | 9/1999 | Anderson et al. |
| 5,984,864 A | 11/1999 | Fox et al. |
| 6,010,531 A | 1/2000 | Donion et al. |
| 6,013,027 A | 1/2000 | Khan et al. |
| 6,015,378 A | 1/2000 | Borst et al. |
| 6,019,722 A | 2/2000 | Spence et al. |
| 6,027,476 A | 2/2000 | Sterman et al. |
| 6,029,671 A | 2/2000 | Stevens et al. |
| 6,036,641 A | 3/2000 | Taylor et al. |
| 6,042,539 A | 3/2000 | Harper et al. |
| 6,050,266 A | 4/2000 | Benetti et al. |
| 6,110,187 A | 8/2000 | Donlon |
| 6,120,436 A | 9/2000 | Anderson et al. |
| 6,139,492 A | 10/2000 | Vierra et al. |
| 6,149,583 A | 11/2000 | Vierra et al. |
| 6,183,486 B1 | 2/2001 | Snow et al. |
| 6,210,323 B1 | 4/2001 | Gilhuly et al. |
| 6,213,940 B1 | 4/2001 | Sherts et al. |
| 6,213,941 B1 | 4/2001 | Benetti et al. |
| 6,231,585 B1 | 5/2001 | Takahashi et al. |
| 6,251,065 B1 | 6/2001 | Kochamba |
| 6,264,605 B1 | 7/2001 | Scirica et al. |
| 6,315,717 B1 | 11/2001 | Benetti et al. |
| 6,346,077 B1 | 2/2002 | Taylor et al. |
| 6,350,229 B1 | 2/2002 | Borst et al. |
| 6,371,906 B1 | 4/2002 | Borst et al. |
| 6,371,910 B1 | 4/2002 | Zwart et al. |
| 6,375,611 B1 | 4/2002 | Voss et al. |
| 6,394,951 B1 | 5/2002 | Taylor et al. |
| 6,398,726 B1 | 6/2002 | Romans et al. |
| 6,406,424 B1 | 6/2002 | Williamson et al. |
| 6,447,443 B1 | 9/2002 | Keogh et al. |
| 6,458,079 B1 | 10/2002 | Cohn et al. |
| 6,464,629 B1 | 10/2002 | Boone et al. |
| 6,464,630 B1 | 10/2002 | Borst et al. |
| 6,468,265 B1 | 10/2002 | Evans et al. |
| 6,478,029 B1 | 11/2002 | Boyd et al. |
| 6,478,729 B1 | 11/2002 | Rogers et al. |
| 6,482,151 B1 | 11/2002 | Vierra et al. |
| 6,494,211 B1 | 12/2002 | Boyd et al. |
| 6,503,245 B2 | 1/2003 | Palmer et al. |
| 6,506,149 B2 | 1/2003 | Peng et al. |
| 6,537,212 B2 | 3/2003 | Sherts et al. |
| 6,565,508 B2 | 5/2003 | Scirica et al. |
| 6,589,166 B2 | 7/2003 | Knight et al. |
| 6,592,573 B2 | 7/2003 | Castaneda et al. |
| 6,602,183 B1 | 8/2003 | Levi et al. |
| 6,607,479 B1 | 8/2003 | Kochamba et al. |
| 6,610,008 B1 | 8/2003 | Spence et al. |
| 6,610,009 B2 | 8/2003 | Person |
| 6,730,020 B2 | 5/2004 | Peng et al. |
| 6,733,445 B2 | 5/2004 | Hinchliffe et al. |
| 6,743,169 B1 | 6/2004 | Taylor et al. |
| 6,890,292 B2 | 5/2005 | Kachamba et al. |
| 6,899,670 B2 | 5/2005 | Peng et al. |
| 6,902,523 B2 | 6/2005 | Kachamba et al. |
| 6,936,002 B2 | 8/2005 | Kachamba et al. |
| 7,056,287 B2 | 6/2006 | Taylor et al. |
| 7,226,409 B2 | 6/2007 | Peng et al. |
| 7,766,817 B2 * | 8/2010 | Peng et al. .................. 600/37 |

FOREIGN PATENT DOCUMENTS

| | | |
|---|---|---|
| DE | 4139695 A1 | 6/1993 |
| EP | 0 820 721 A1 | 7/1997 |
| EP | 0 791 329 A1 | 8/1997 |
| EP | 0 791 330 A2 | 8/1997 |
| EP | 0 808 606 A1 | 11/1997 |
| EP | 0820721 A1 | 1/1998 |
| EP | 0 919 193 A1 | 6/1999 |
| WO | WO 96/40354 | 12/1996 |
| WO | WO 97/10753 | 3/1997 |
| WO | WO 97/26828 | 7/1997 |
| WO | WO 97/40738 | 11/1997 |
| WO | WO 98/37814 A1 | 9/1998 |
| WO | WO 98/49944 | 11/1998 |
| WO | WO 99/60929 | 12/1999 |
| WO | WO 99/60930 | 12/1999 |
| WO | WO 00/10466 | 3/2000 |
| WO | WO 01/17437 A3 | 3/2001 |

OTHER PUBLICATIONS

Grundeman et al., "Hemodynamaic Changes During Displacement of the Beating Heart by the Utrecht Octopus Method," Ann Thorac Surg. 1997;63:S88-92.

Jansen et al., "Off-Pump Coronary Bypass Grafting: How to Use the Octopus Tissue Stabilizer," Ann Thorac Surg. 1998; 66:576-9.

Jansen et al., "Experimental Off-Pump Grafting of a Circumflex Branch via Sternotomy Using a Suction Device," Ann Thorac Surg. 1997; 63:S93-6.

Angelini, G.D., "A Simple, Inexpensive Method of Heart Retraction During Coronary Artery Bypass Surgery," Ann Thorac Surg. 1998; 46:246-247.

Calvin, I.F. & Newman, D.C., "Circumflex Exposure Using a Cardiac Sling," Ann Thorac Surg. 1990; 49:833-4.

Splittgerber et al., "Exposing the Circumflex Coronary Artery: The Heartflip Technique," Ann Thorac Surg. 1996; 61:1119-20.

Rousou et al., "Cardiac Retractor for Coronary Bypass Operations," Ann Thorac Surg. 1991; 52:877-8.

Matsuura et al., "A New Device for Exposing the Circumflex Coronary Artery," Ann Thorac Surg. 1995; 59:1249-50.

Janke, Walter H., "Heart Support for Coronary Bypass Surgery Involving the Circumflex Artery System," The Journal of Thoracic and Cardiovascular Surgery, Feb. 11, 1974, pp. 883-884.

Kazama, Shigeru, & Ishihara, Akira., "Fabric Heart Retractor for Coronary Artery Bypass Operations," Ann Thorac Surg. 1993; 55:1582-3.

Takahashi et al., "A New Instrument for Immobilization and Hemostasis During Minimally Invasive Direct Coronary Artery Bypass ('MIDCAB doughnut'): Experimental Study," J Card Surg. 1997;12:185-189.

Borst et al., "Coronary Artery Bypass Grafting Without Cardiopulmonary Bypass and Without Interruption of Native Coronary Flow Using a Novel Anastomosis Site Restraining Device ('Octopus')," JAAC vol. 27, No, 6 May 1996:1356-64.

* cited by examiner

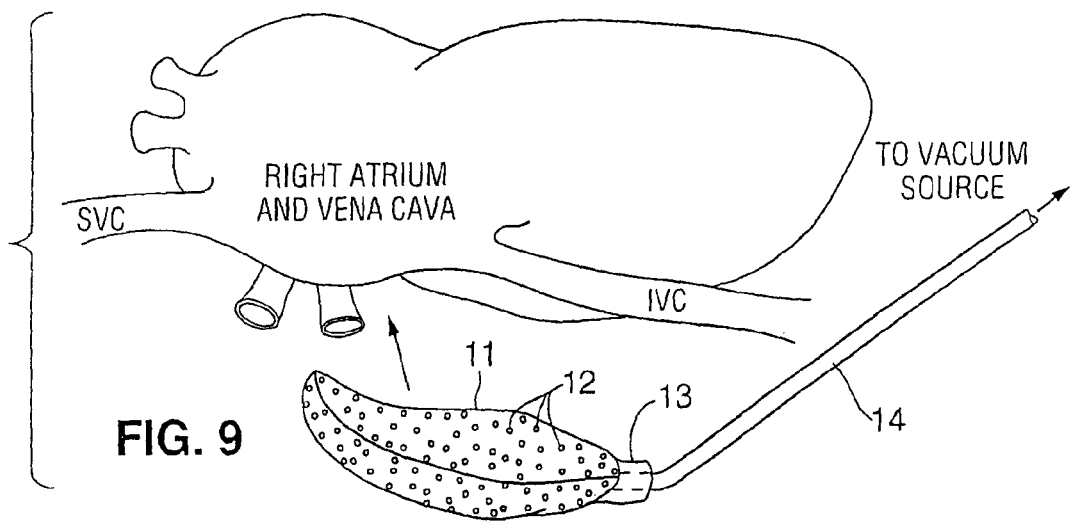
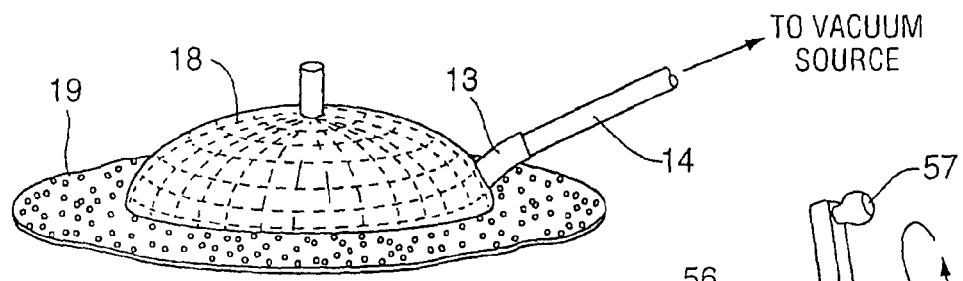
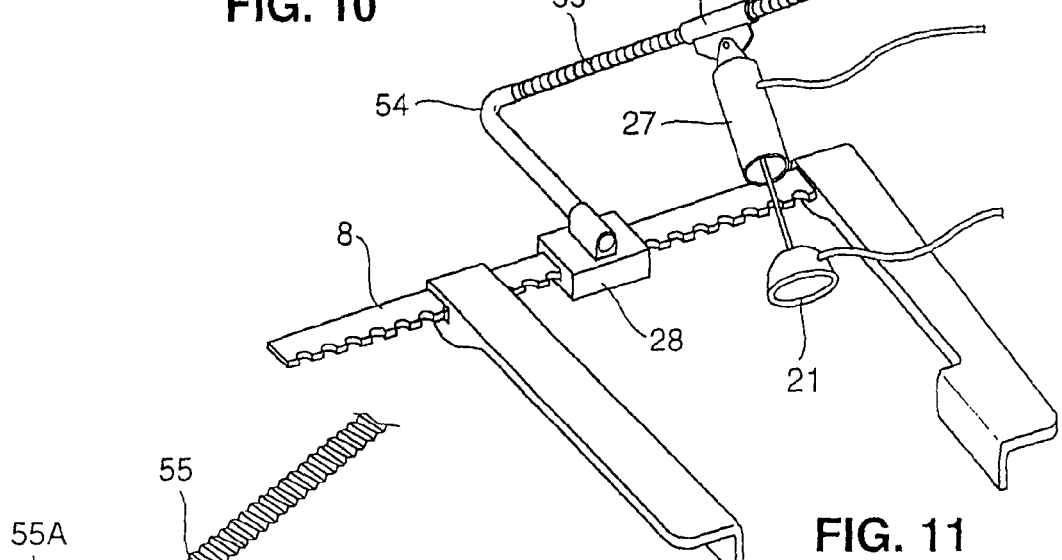
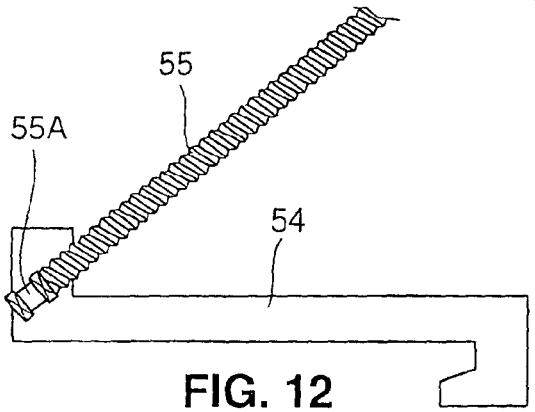

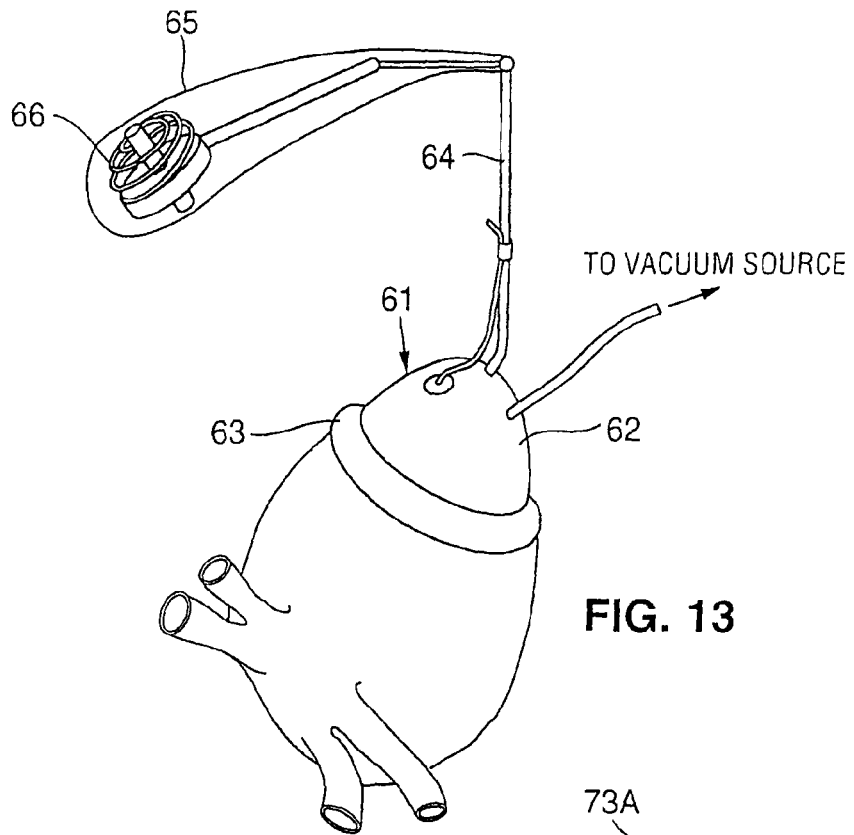
FIG. 13
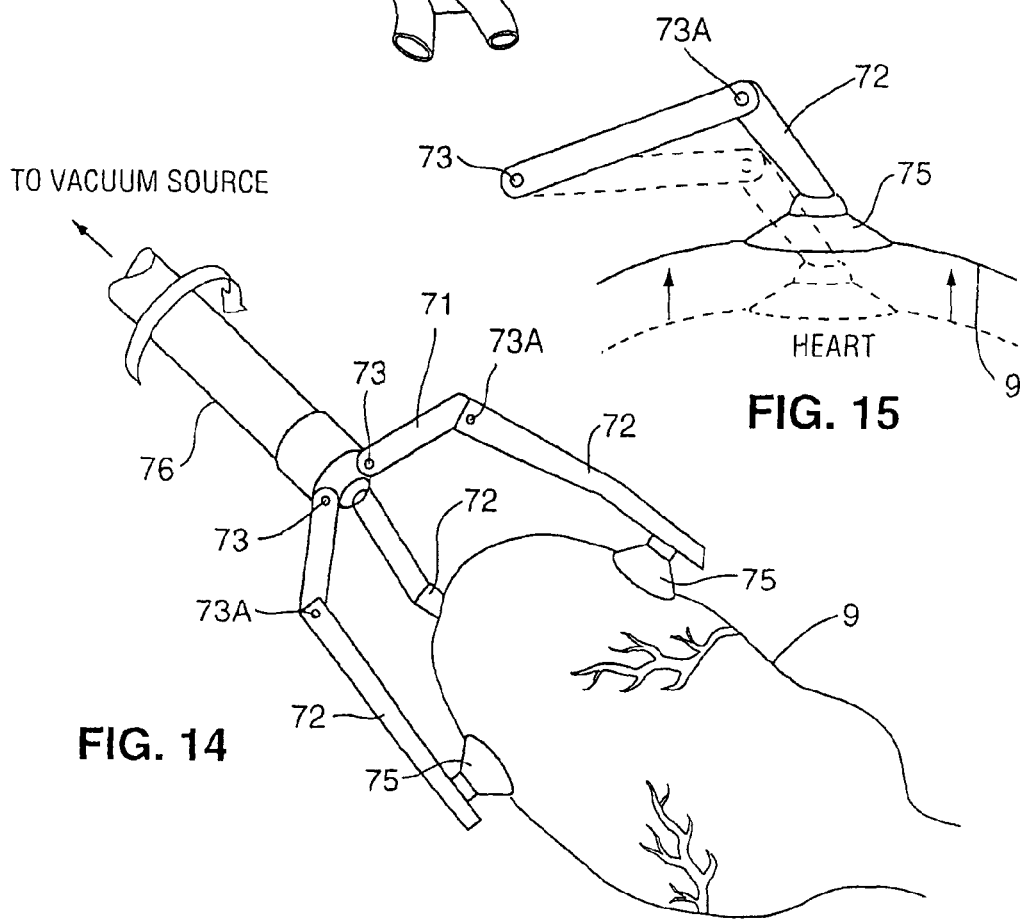
FIG. 14
FIG. 15

ORGAN MANIPULATOR HAVING SUCTION MEMBER SUPPORTED WITH FREEDOM TO MOVE RELATIVE TO ITS SUPPORT

This application is a continuation of application Ser. No. 11/789,383, which is a continuation of application Ser. No. 10/801,024 filed Mar. 15, 2004, now U.S. Pat. No. 7,226,409, which is a continuation of application Ser. No. 09/747,388 filed Dec. 22, 2000, now U.S. Pat. No. 6,730,020, which is a division of application Ser. No. 09/390,792 filed Sep. 7, 1999, now U.S. Pat. No. 6,506,149. application Ser. Nos. 11/789, 383; 10/801,024; 09/747,388; and 09/390,792 and U.S. Pat. Nos. 7,226,499; 7,730,020 and 6,506,149 are hereby incorporated herein, in their entireties, by reference thereto. Further, we claim priority under 35 USC §120 to application Ser. Nos. 11/789,383; 10/801,024; 09/747,388 and 09/390,792.

FIELD OF THE INVENTION

The invention pertains to an apparatus for manipulating (and supporting in a retracted position) an organ such as a beating heart. Preferred embodiments of the invention pertain to an apparatus for support and manipulation of a beating heart during surgery thereon, in a manner promoting oxygenation during the surgery.

BACKGROUND OF THE INVENTION

Coronary artery bypass grafting (CABG) has traditionally been performed with the use of a cardiopulmonary bypass (CPB) machine to oxygenate and perfuse the body during surgery. Recently, techniques have been developed to allow for performing CABG without the use of CPB by stabilizing the epicardial surface of a beating heart at the coronary anastomotic site with a stabilizer (e.g., stabilizing feet) to allow placement of sutures through the graft vessel and recipient coronary artery. This procedure may be performed through a partial or full sternotomy, or via a thoracotomy (which an incision between two adjacent ribs).

Access to the left anterior descending (LAD) coronary artery is easily performed by either a sternotomy or a thoracotomy. However, the patient typically requires bypass to multiple coronary arteries, including the circumflex artery (CxA) on the left lateral aspect of the heart, the right coronary artery (RCA) on the right lateral aspect of the heart, and the posterior descending artery (PDA) on the back side of the heart. It is very difficult to access the CxA, RCA, and PDA without a sternotomy, as the heart needs to be turned or tilted (or turned and tilted) significantly to reach its side or back, and with an intact sternum, insufficient space exists for these maneuvers. For example, the apex of the heart is generally lifted out of the body through a sternotomy in order to reach the PDA. Surgeons often place the patient in a Trendelenberg position, with the operating table tilted so that the patient's head lies lower than the feet with the patient in supine position, in order to assist with lifting the heart up and back.

An additional challenge to beating heart surgery is that some hearts do not tolerate manipulation well from a hemodynamic standpoint. The potential exists with current manipulation techniques to compress the heart (e.g., by pressing it with stabilization feet) or great vessels in such a way that hemodynamic function is compromised.

There is a need for a beating heart retraction apparatus capable of physically translating a beating heart from its natural resting place to a location better suited to surgical access, and then holding the beating heart in the latter location during surgery without compressing (or otherwise deforming) the heart or great vessels in such a way that hemodynamic function is compromised.

Typically, beating heart surgery has been accomplished through a partial sternotomy using pericardial sutures to retract the heart into the proper position for surgery, and using a stabilization apparatus (e.g., stabilizing feet) to stabilise the portion of the heart surface to be cut. Sometimes, surgery is performed on the properly positioned heart without using a stabilization apparatus.

However, conventional use of pericardial sutures for retraction of a beating heart has limitations and disadvantages including the following. It is inconvenient and potentially harmful to the patient to incise the pericardium and insert sutures along cut edges of the pericardium, and then exert tension on the sutures to move the heart together as a unit with the pericardium. When the sutures are pulled to lift the heart (with pericardium), compressive force exerted by the pericardium on at least one side of the heart sometimes constrains cardiac contraction and expansion.

There are three distinct stages involved in preparing an artery (on an organ) for anastomosis:

1. gross manipulation: the organ is physically translated from its natural resting place to a location better suited to surgical access;

2. artery presentation: the target artery on the organ is identified and the position of the organ is finely adjusted so that the target artery is approachable; and 3. artery stabilization: the target artery and surrounding tissues are immobilized, allowing fine surgical techniques on very small features.

The present invention pertains to an improved method and apparatus for retraction (gross movement) of a beating heart or other organ into a desired position and orientation to allow surgery to be performed on the organ. When the organ has been retracted (in accordance with the invention) into a desired position and orientation, any of the many commercially available tissue stabilization products (including those marketed by Guidant, Medtronic, CardioThoracic Systems, and Ethicon) can be used to stabilize a portion of the organ's surface on which surgery is to be performed. However, such tissue stabilization products cannot duplicate the function of the inventive apparatus. Retraction requires lifting and usually rotation of the organ. Devices designed specifically for tissue stabilization are not well suited to those motions.

One class of the stabilization devices commonly used to stabilize a target portion of a heart surface (a portion on which surgery is to be performed) are the stabilization devices that comprise rigid (C-shaped or linear) structures lined with suction cups, such as those described in the article Borst, et al., "Coronary Artery Bypass Grafting Without Cardiopulmonary Bypass and Without Interruption of Native Coronary Flow Using a Novel Anastomosis Site Restraining Device ("Octopus"), J. of the American College at Cardiology, Vol. 27, No. 6, pp. 1356-1364, May 1996. The stabilization devices described in the Borst, et al. article are marketed by Medtronic, Inc. and are known as "Octopus" devices.

It has been proposed to use such an Octopus device to retract the heart into a desired position for surgery (and hold the retracted heart in this position), as well as to stabilize a portion of the heart's surface following retraction (gross movement) of the heart. See, for example, PCT International Application WO97/10753 (by Medtronic, Inc.) entitled "Method and Apparatus for Temporarily Immobilizing a Local Area of Tissue," published Mar. 27, 1997, especially with reference to FIG. 33 thereof. However, no conventional Octopus device can support a beating heart with adequate compliance to allow normal heart beating movement, and instead each conventional Octopus device would exert compressive or twisting force on at least one side of the beating heart, thereby constraining cardiac contraction and expansion. Also, one of the small-diameter suction cups of a conventional Octopus device would be too small to reliably grip (and support) the heart without causing trauma to the heart surface. Thus, in order to reliably (but atraumatically) retract and support the heart in the retracted position, many small-diameter suction cups (supported on a rigid frame which frame is itself rigidly supported) need to exert suction simultaneously on the heart, which exacerbates the problem of constrained cardiac contraction and expansion due to the exertion of compressive or twisting force on the heart.

The apparatus of the invention differs in purpose and form from conventional tissue stabilization devices. The purpose of the inventive apparatus is to move an organ grossly from one position to another and maintain the organ in the final position (without significantly constraining cardiac contraction and expansion). The inventive apparatus is not designed to stabilize specific areas of the organ. The shape and nature of the suction cup (or other suction member) of the inventive apparatus differ from the suction cups of conventional tissue stabilization devices in the need to accommodate different anatomy. For example, the inventive suction member can be larger than a conventional tissue stabilization device. Also, since the inventive apparatus exerts suction over a larger surface area of organ tissue, the required pressure differential can be less than that required by conventional tissue stabilization devices. The low-pressure differential has a clinical benefit in that the potential for creation of hematomas is lessened.

U.S. Pat. No. 5,799,661, issued Sep. 1, 1999 to Boyd, et al. (and assigned to Heartport, Inc.) describes (with reference to FIGS. 33A-33C) a suction cup manipulator on a long shaft. The suction cup is to be attached to an arrested heart by suction, and the device is then manipulated to move the heart around in the chest cavity. A vacuum is applied to the cup to provide suction, and the vacuum is said preferably to have a value not less than −150 mmHg (to avoid tissue damage). The suction cup is made of a soft, flexible elastomeric material such as silicone rubber, has a diameter of approximately 12 mm to 50 mm, and has a textured, high friction distal surface (for gripping the heart). The high friction can be achieved by a pattern of bumps or an absorbent high friction material (such a nonwoven polyester fabric). A disadvantage of the bumps is that they would likely cause trauma to the organ being manipulated (even with a vacuum in the preferred range).

U.S. Pat. No. 5,799,661 suggests without explanation that the suction cup is flexibly mounted to the distal end of a rigid shaft, but it is apparent from FIGS. 33A-33B that this simply means that the cup itself has some flexibility so that the cup can bend relative to the rigid shaft. U.S. Pat. No. 5,799,661 does not teach attaching the suction cup to the shaft by a joint which provides limited freedom to translate along a first axis and/or full (or at least limited) freedom to rotate about the first axis, but no significant freedom to translate in directions perpendicular to the first axis. Thus, the suction cup apparatus described in U.S. Pat. No. 5,799,611 is useful only to retract an arrested heart; not a beating heart or other moving organ since the suction cup apparatus of U.S. Pat. No. 5,799,611 does not have compliance to allow for normal organ movement such as a heart beat, and would instead exert compressive or twisting force on at least one side of the moving organ, thereby constraining cardiac contraction and expansion or other normal organ movement.

U.S. Pat. No. 5,782,746, issued Jul. 21, 1998, discloses an annular suction device for immobilizing part of the surface of a heart during surgery. Although the device is said to allow the heart to beat in a "relatively normal" manner during surgery, the device is rigidly mounted to a fixed mounting structure during surgery, and thus neither the device nor the part of the heart surface which it immobilizes would have freedom to move significantly relative to the mounting structure during surgery. The reference suggests positioning the device on the heart, applying vacuum to the device to cause it to exert suction on the heart, then moving the device to "partially" raise the heart, and then rigidly mounting the device to the fixed mounting structure so that the device supports the "partially raised" heart during surgery.

A key difference between the inventive apparatus and both conventional apparatus for tissue stabilization and conventional apparatus for organ retraction is that the inventive apparatus provides system compliance that allows the target organ to maintain normal motion (e.g., normal compression and expansion in the case that the organ is a beating heart). In the case of a beating heart, this compliance provides distinct clinical value by lessening the negative impact of manipulation on hemodynamics.

SUMMARY OF THE INVENTION

In a class of embodiments, the invention is an organ manipulator including at least one suction member (e.g., a suction cup) and preferably also a compliant joint to which the suction member is mounted. The compliant joint provides built-in system compliance so that when the suction member supports an organ (e.g., a beating heart) by suction, the suction member does not constrain normal motion of the organ (e.g., normal beating motion of the heart), either during gross movement of the organ into a retracted position or during surgery with the organ attached to or held by the suction member in the retracted position. In preferred embodiments the suction member is shaped and configured to retract a beating heart and suspend it in the retracted position during surgery. As the suspended heart beats, the compliant joint allows the heart to expand and contract freely (and otherwise move naturally) so that hemodynamic function is not compromised. Suspension of the beating heart below the suction member tends to expand the heart chambers, which in turn tends to reduce the amount of compressive deformation of the heart and great vessels which would otherwise result from pressing the heart with a stabilization device (such as stabilization feet) during surgery, so that the invention assists in oxygenation during surgery.

The suction member conforms (or, in some embodiments can be deformed to conform) to the anatomy of the organ. Preferably, its inner surface is smooth, concave, and lined with absorbent material to improve traction without causing trauma to the organ (e.g., bruising) during retraction from one position to another within the body cavity. Preferably, the suction member is a suction cup having a foam seal mounted around the cup's periphery.

Coupling a vacuum source to the suction member (with the member applied to the organ surface) crates a differential in pressure between the inner and outer surfaces of the member. The pressure differential forces the suction member and organ surface together in such a manner as to create traction between the two. As a result of the traction, the surface of the organ will move with the suction member. The device holds the organ with sufficient force to allow retraction using suction, and to maintain the organ in the desired position (i.e., suspending it from the suction member) during surgery.

In preferred embodiments, the compliant joint couples the suction member to an arm (which is rigid or can be placed in a rigid state), and the arm is adjustably mounted to a fixed mounting structure. The mounting structure can be a conventional sternal retractor (of the type used to maintain a sternal incision in an open state for cardiac access), an operating table, or another rigid structure. When the organ is attached to or held by (e.g., suspended below) the suction member, the compliant joint gives the suction member freedom to move (at least axially along the axis of the suction member, e.g., vertically when the suction member has a vertical axis) relative to the arm and mounting structure in response to normal, organ movement (e.g., beating of a heart) to avoid compromising the normal functioning of the organ. When a beating heart is suspended below the suction member, the compliant joint allows the heart to expand and contract freely (at least vertically) as it beats. Optionally, the compliant joint also gives the organ freedom to rotate about the axis of the suction member (typically, a vertical axis) and/or to swing relative to the arm.

In preferred embodiments, the inventive apparatus provides for compliant retraction of a beating heart (or other organ) in the sense that it retracts the organ via suction, while allowing normal myocardial movement (or other normal organ movement) in at least the vertical direction, and optionally also allowing normal organ movement perpendicular to the vertical direction (e.g., pivoting or twisting motion about a vertical axis). In some such preferred embodiments, the compliant joint is a sliding ball joint attached to a movable arm, and the arm can be locked in any of a variety of positions (relative to a fixed supporting structure) to allow adjustable degrees of organ retraction. The compliance provided by the ball joint allows the organ to better tolerate manipulation.

Preferably, the suction member is specially designed to decrease trauma to the heart muscle (or other organ tissue) during attachment, and the apparatus is preferably implemented to have one or more of the following features: an absorbent cup lining for increased holding power, a smooth and soft inner cup surface to decrease myocardial bruising (hematoma formation) and to diffuse the suction across the cup, a means for regulation of suction intensity, and a vacuum accumulator in the suction line to decrease immediate loss of holding power with variations in vacuum supply.

In other embodiments, the inventive apparatus includes multiple suction members (e.g., multiple suction cups) mounted on the ends of retracting fingers for gripping an organ, with the fingers implementing a compliant joint. In other alternative embodiments, the inventive apparatus includes a bio-absorbable disc with an adhesive surface to be adhered to the heart or other organ (instead of a suction member), with the disc preferably being mounted to a compliant joint.

In other embodiments, the invention is a method for compliant retraction of an organ, including the steps of retracting the organ using suction, and supporting the organ in the retracted position using suction, in such a manner that the organ has freedom to move normally (e.g., to beat or undergo other limited-amplitude motion) at least in the direction in which the suction is exerted during both steps. In some such embodiments, the method includes the steps of retracting the organ using suction, and suspending the organ in the retracted position using suction, in such a manner that the organ has freedom to move normally (e.g., to beat or undergo other limited-amplitude motion) in at least the vertical direction during both steps. One embodiment is a method for retracting a beating heart, including the steps of affixing a suction member (e.g., a suction cup) to the heart at a position concentric with the apex of the heart (preferably the suction member has sufficient curvature to conform with the apex and is shaped to be at least generally symmetric with the apex) and applying suction to the heart (e.g., by coupling the suction member to a vacuum source), and moving the suction member to retract the heart to a desired position for surgery such that the heart has freedom to undergo normal beating motion (at least along the axis of the suction member) during retraction. Preferably, the suction member is mounted to a fixed assembly (e.g., a fixedly mounted sternal refractor) by a compliant joint in such a manner that the suction member does not constrain normal beating motion of the heart, either during gross movement, of the member (with heart) into the desired position or while the heart is supported by (e.g., suspended vertically below) the member during surgery in such position. In such preferred embodiments, as the heart beats, it is free to expand and contract normally (with the compliant joint allowing the suction member to oscillate along the axis of the suction member, and optionally also to twist about such axis) so that hemodynamic function is not compromised.

Other aspects of the invention are a flexible locking attachment arm (having both a flexible state and a rigid state) to which the inventive suction member (or compliant joint) is mounted, and an organ manipulator including such a locking arm and at least one suction member (or compliant joint and suction member) mounted to the arm.

BRIEF DESCRIPTION OF THE DRAWINGS

FIG. 9 is a perspective view of a portion of another alternative embodiment of the inventive organ manipulation apparatus.

FIG. 10 is a perspective view of a portion of a variation on the FIG. 9 embodiment.

FIG. 11 is a perspective view of a portion of another preferred embodiment of the inventive organ manipulation apparatus.

FIG. 12 is a more detailed perspective view (partially cut away to show element 55A) of a portion of the FIG. 11 embodiment.

FIG. 13 is a perspective view of a portion of another alternative embodiment of the inventive organ manipulation apparatus.

FIG. 14 is a perspective view of a portion of another alternative embodiment of the inventive organ manipulation apparatus, which employs hinged fingers and multiple suction cups.

FIG. 15 is a perspective view of one finger 72 of the FIG. 14 apparatus gripping the surface of heart 9, and shows (in phantom view) the position the finger would have if the heart surface were in a lower position.

FIG. 35 is a cross-sectional view of the sleeve of FIG. 35, taken along line 36-36 of FIG. 35.

DETAILED DESCRIPTION OF THE PREFERRED EMBODIMENTS

Throughout this disclosure, including in the claims, the expression "compliant joint" is used in a broad sense to denote any mechanical coupling capable of bearing the load of the inventive suction member (and file organ attached by suction to the suction member) while allowing the suction member (and organ) freedom to move in the described manner. The compliant joint can be implemented in any of a wide variety of ways, including (but not limited to) a sliding ball joint, a hinged joint, a pin which slides in a slot, a universal joint, or a spring assembly in which the spring constant is determined by a bellows, piston, metal spring, or some other compliant element).

A first preferred embodiment of the invention will be described with reference to FIG. 1.

Figure 1:
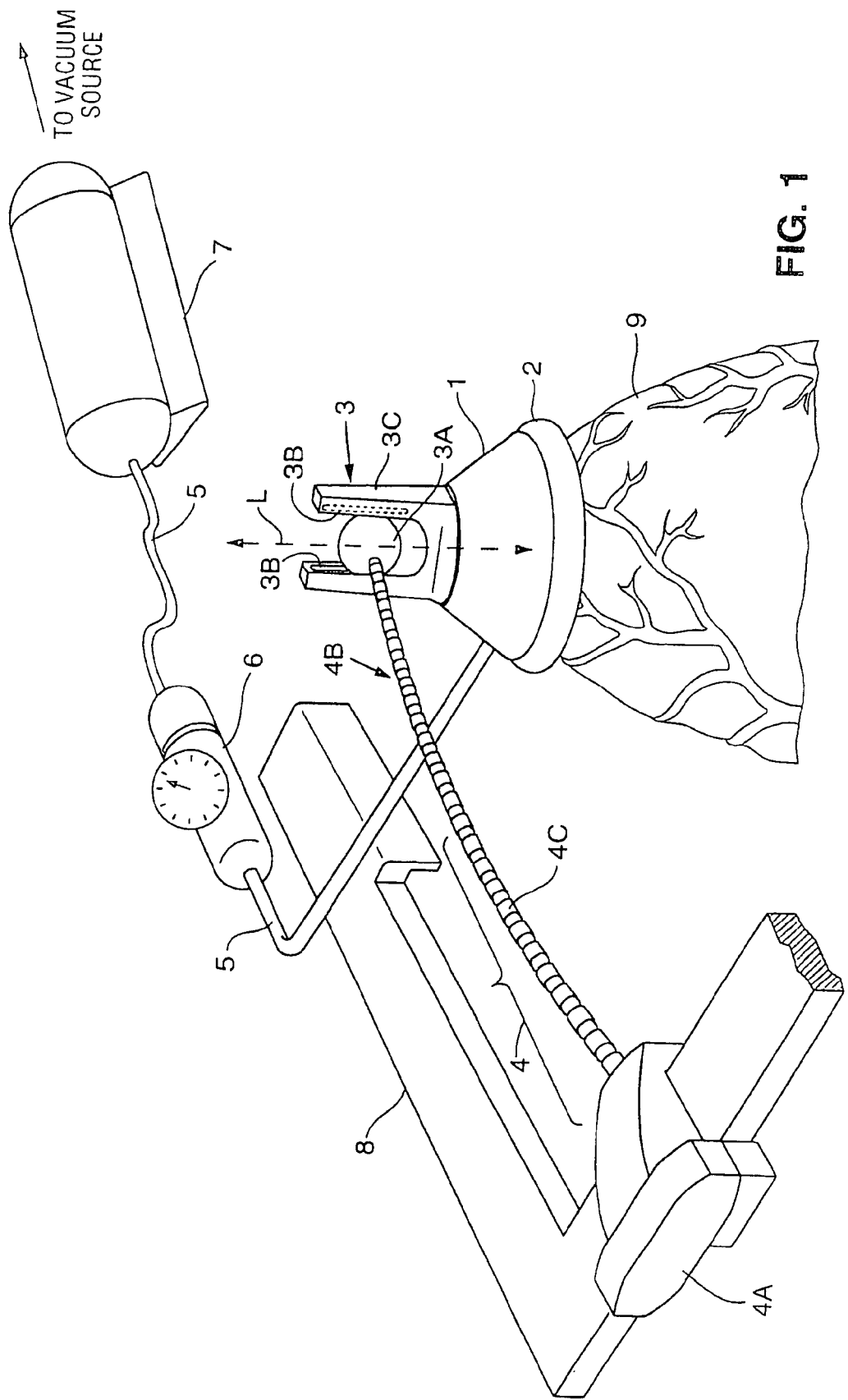
FIG. 1 is a perspective view of a preferred embodiment of the inventive organ manipulation apparatus.

The FIG. 1 embodiment is designed to retract heart 9 (by exerting suction) to a position suitable for performing surgery thereon, and to retain heart 9 in the retracted position (by continued exertion of suction thereon) with limited freedom to move. In the FIG. 1 embodiment, the inventive apparatus includes the following main elements: suction cup 1 (including conforming seal 2 which extends around the periphery of cup 1), ball sliding joint assembly 3, flexible locking attachment arm 4 (which has both a rigid and a flexible state), suction line 5, suction flow regulator 6, and vacuum accumulator 7.

We will denote the surface of the inventive suction cup (e.g., cup 1 of FIG. 1 or cup 1A of FIG. 2) which contacts the organ to be retracted as the "inner" surface of the suction cup.

Preferably, the inner surface of suction cup 1 is concave, and is shaped (or can be shaped) so that cup 1 can be attached directly to the apex of heart 9 as shown with seal 2 conforming to the heart surface at the apex, so that cup 1 can lift the heart by exerting suction thereon. In some preferred embodiments cup 1 is not flexible (except for seal 2), but in other preferred embodiments it is flexible. In some preferred embodiments, cup 1 is implemented to be flexible but to have a shape memory, such as by forming the cup of metal mesh (which can assemble chicken wire) coated with a continuous sheet of silicone rubber (and then attaching seal 2 around its periphery). In embodiments having a shape memory, the user can deform the cup (e.g., by pressing it with his or her fingers) to conform the cup to fit against any of a variety of different portions of an organ (or against any of a variety of different organs) and the cup will remain in the selected shape until later deformed by the user.

In all embodiments, conforming seal 2 forms a seal with heart 9 (or another organ) while also preventing the organ tissue from being sucked substantially into the internal area of the cup. Conforming seal 2 is preferably made of biocompatible foam that is glued to the remaining portion of cup 1. In a class of preferred embodiments, seal 2 is identical to seal 35 of cup 1A (to be described below with reference to FIGS. 2, 3, and 4).

With reference to FIG. 1, the body of suction cup 1 is preferably made of flexible material (e.g., elastomeric material having no shape memory, or a continuous sheet of elastomeric material coated over a deformable metal mesh which has a shape memory), and its inner surface is preferably lined with a soft and absorbent material (not shown in FIG. 1). The absorbent lining can be a biocompatible fabric (preferably non-woven rayon/viscose fabric), gauze, or material of the type currently used in neuro-sponges, and is capable of absorbing enough blood and/or other bodily fluid to significantly improve traction between the cup and the organ. The absorbent lining also functions to diffuse the suction.

In alternative embodiments, the inner surface of cup 1 is implemented with compliant cleats protruding out therefrom, or is otherwise textured so as to assist in providing grip on the organ tissue.

In any embodiment of the invention, the inner surface of the suction cup (e.g., cup 1) is gas-permeable (e.g., porous, or having at least one orifice extending through it). The pores are (or the orifice is) in fluid communication with a vacuum source. Thus, when the vacuum source is active a large surface area of the organ is sucked by the vacuum against the cup's inner surface, with a suction force sufficient to overcome gravity to allow the organ to be moved grossly to a desired position by moving the suction cup (or an element to which the suction cup is mounted).

Suction is provided to suction cup 1 by means of flexible suction line 5. The distal end of line 5 is in fluid communication with the pores (or orifice) through the inner surface of cup 1, and the proximal end of line 5 is in fluid communication with suction flow regulator 6. The suction flow rate is controlled by flow regulator 6. Vacuum accumulator 7 is coupled to flow regulator 6, and serves as a low-pressure reservoir having sufficient volume that it can provide suction in the event of an interruption of regular suction flow from a vacuum source (not shown, but which can be a wall source).

In preferred implementations for use in retracting a human heart, suction cup 1 has a diameter (at its outer periphery) greater than about one inch (25.4 mm), and the vacuum provided by the vacuum source is in the range from −7 psi to −5 psi (−362 mmHg to −258 mmHg). For a particular application, the vacuum provided by the vacuum source should be determined (e.g., experimentally) to be as close as possible to atmospheric pressure while still providing enough suction force to reliably grip the organ to be retracted.

Ball sliding joint 3 (which includes ball 3A and U-shaped element 3C) connects suction cup 1 to flexible locking attachment arm 4. As shown in FIG. 1, one end of flexible locking attaching arm 4 is attached to sternal retractor 8 (this end can alternatively be attached directly to an operating table) and the other end of arm 4 is attached to ball sliding joint 3. Ball 3A rides in grooves 3B of element 3C. Cup 1 is mounted rotatably to element 3C (e.g., by a binding screw which couples them together), so that when element 3C is oriented with grooves 3B vertical (as shown in FIG. 1), cup 1 can rotate freely about a vertical axis relative to element 3C. Thus, joint 3 allows cup 1 (and heart 9) to rotate about a vertical axis relative to arm 4 and retractor 8 (as ball 3A rotates relative to element 3C). Joint 3 also allows cup 1 (and heart 9) limited freedom to translate up and down (along the central longitudinal axis L of cup 1, which is oriented vertically in FIG. 1) relative to retractor 8 (as vertical grooves 32, slide up and down relative to ball 3A) thereby providing compliance to the system. As heart 9 beats, its outer surface expands and contracts (which causes cup 1 and element 3C to oscillate vertically relative to stationary ball 3A) and its apex may twist about a vertical axis relative to ball 3A and arm 4.

The FIG. 1 apparatus can be oriented so that arm 4 does not extend in a horizontal plane (relative to the earth). Regardless of the orientation of arm 4, when cup 1 supports an organ, element 3C will rotate relative to ball 3A until grooves 3B are vertical.

Flexible (Locking attachment arm 4 is designed to have both a flexible state and a rigid state. In a preferred implementation, this is achieved by implementing free portion 4B of arm 4 (in a conventional manner) to include a cable running from mount 4A through a series of ball joints 4C (or alternating ball joints and sleeves), so that portion 4B can be changed between a flexible state and a rigid state by tightening (or untightening) the cable using a knob mechanism with a clutch. The clutch guards against overtightening of the assembly, and provides tactile feedback when the maximum tightening is achieved. Preferred implementations of ball joints (or ball joints and sleeve) for use in arm 4 will be described below, with references to FIGS. 32-38.

The pressure at the inner surface of cup 1 is reduced by opening suction flow regulator 6, thus enabling cup 1 to provide suction. In operation, cup 1 is placed against the appropriate portion of heart 9, (for example, on the heart's apex as shown in FIG. 1) either before or after flow regulator 6 is opened, depending on the particular application. When cup 1 is positioned against and providing suction to organ 9, flexible locking attachment arm 4 is manipulated to retract the organ (with cup 1 and ball sliding joint 3) into a desired position. Specifically, flexible locking attachment arm 4 is moved (e.g., by translating mount portion 4A along member 8, and/or placing free portion 4B in a flexible state and bending free portion 4B) to manipulate organ 9 into the desired position. Ball sliding joint 3 permits cup 1 to pivot relative to free portion 4B of arm 4 (and ball 3A to translate along grooves 3B) while the organ is manipulated. When the organ is properly positioned, portion 4A of arm 4 is locked to retractor 8 and portion 4B of arm 4 is locked into its fixed state, but ball sliding joint 3 is still configured to provide compliance.

An alternative embodiment of the invention will next be described with reference to FIG. 2. Elements 3, 5, 6, 7, and 8 of the FIG. 2 embodiment are identical to the identically numbered elements of the above-described FIG. 1 embodiment (and the description thereof will not be repeated). Suction cup 1A of FIG. 2 differs slightly from cup 1 of FIG. 1, in that suction line 5 is coupled (through ball 3A and element 3C) to a gas-permeable portion (an orifice or pores) at the center of cup 1A, whereas suction line 5 is coupled to a gas-permeable portion (orifice or pores) of cup 1 at a location away from the center of cup 1.

Figure 2:
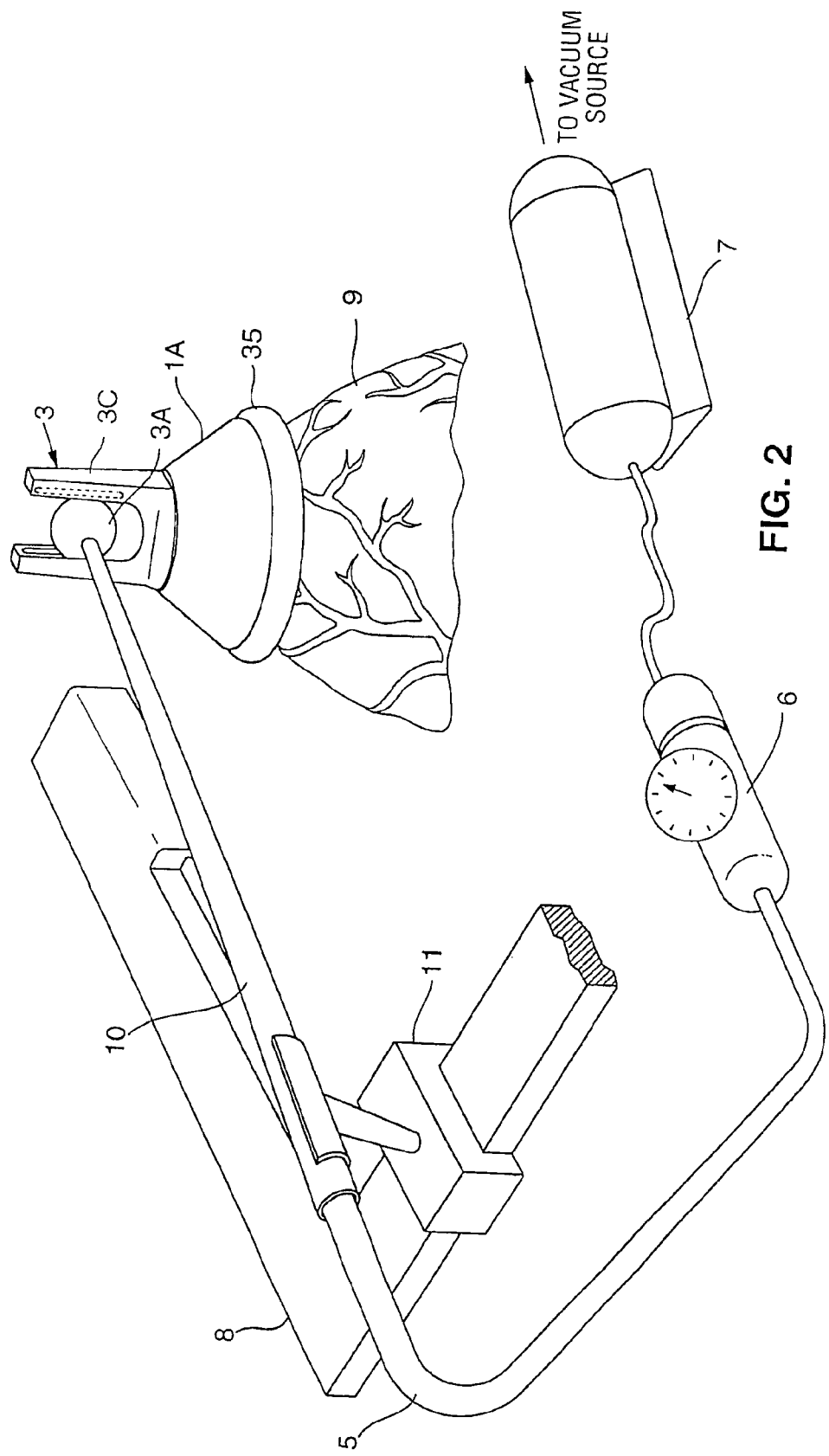
FIG. 2 is a perspective view of another preferred embodiment of the inventive organ manipulation apparatus.

In the FIG. 2 embodiment, rigid arm 10 (which replaces flexible locking arm 4 of FIG. 1) exerts a retracting force upon suction cup 1A. Rigid arm 10 is preferably adjustably mounted to retractor 8 by a standard tool holder 11 (of a type commonly used in the practice of surgery). Rigid arm 10 is hollow, and suction line 5 is routed through rigid arm 10 (and then through ball 3A and element 3C) to cup 1.

Figure 3:
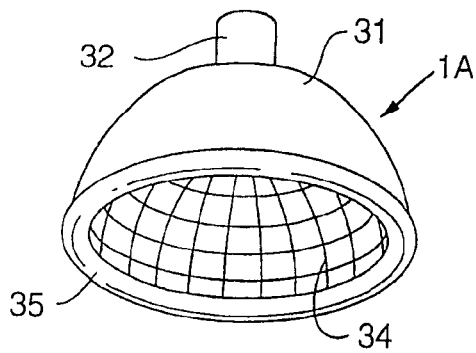
FIG. 3 is a perspective view of another preferred embodiment of suction cup 1A of FIG. 2.
Figure 4:
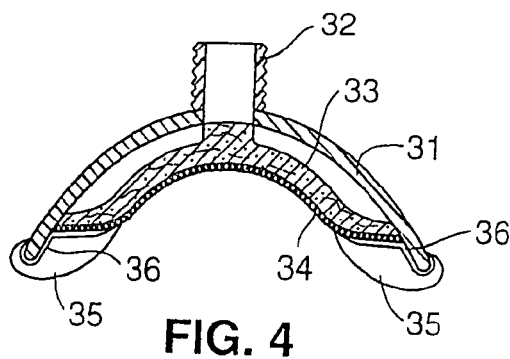
FIG. 4 is a cross-sectional view of the FIG. 3 embodiment of cup 1A.

A preferred embodiment of cup 1A is shown in more detail in FIGS. 3 and 4. In this embodiment, cup 1A has a flexible silicone rubber shell 31 with a generally cylindrical attachment portion 32 that defines a central orifice through the shell. Portion 32 is shaped for attachment to the distal end of line 5. The outer periphery of shell 31 is a mild ellipse (the ratio of its long axis to and short axis is less than two, e.g., the ratio is about 1.45). Absorbent material 33 (e.g., gauze or "bleed" cloth) is loosely packed against shell 31 to absorb blood and other fluid that may be present at the organ surface in order to improve the grip of cup 1A on the organ. Non-abrasive, organ-contacting (e.g., myocardium-contacting) mesh 34 is installed over material 33 to retain the material 33 in the position shown.

Tapered conformal seal 35 (preferably made of biocompatible foam) is glued to the portion of mesh 34 in contact with shell 31 (and to the peripheral portion of shell 31 itself). Specifically, glue 36 is placed on mesh 34 near the periphery of shell 31 (and on shell 31 around its periphery), and foam seal 35 is positioned over glue 36 to glue together the seal 35, mesh 34, and shell 31 as shown. Glue 36 should not extend inward to (or beyond) the inner edge of seal 35, so as to avoid introducing a stiff (hardened glue) surface that would contact the organ during exertion of suction on the organ.

In alternative embodiments of the invention, compliant joint 3 (of FIGS. 1 and 2) is replaced by another type of compliant joint, such as one including a pin which slides in a slot, a bellows, a piston, a spring, or some other compliant element. In one such alternative embodiment (shown in FIG. 5), rigid arm 24 replaces arm 10 (of FIG. 2). The proximal end of arm 24 is attached to sliding mount 28. A second sliding mount 26 attached to arm 24 can be translated to a desired location along arm 24 and then locked into place. Suction cup 21 is attached to the distal end of rigid tube 22 (preferably in such a manner that cup 21 has freedom to rotate about the axis of tube 22), and the distal end of compliant element 27 is attached to the proximal end of tube 22. Suction line 25 is attached to element 27 in such a manner that line 25 is in fluid communication with the interior of tube 22, so that a vacuum source can evacuate line 25 and tube 22 and cause cup 21 to exert suction on organ 9 (a human heart) when cup 21 is positioned as shown against heart 9. The proximal end of element 27 is attached to sliding mount 26 (so that element 27 and tube 22 have freedom to pivot together as a unit relative to mount 26).

Figure 6:
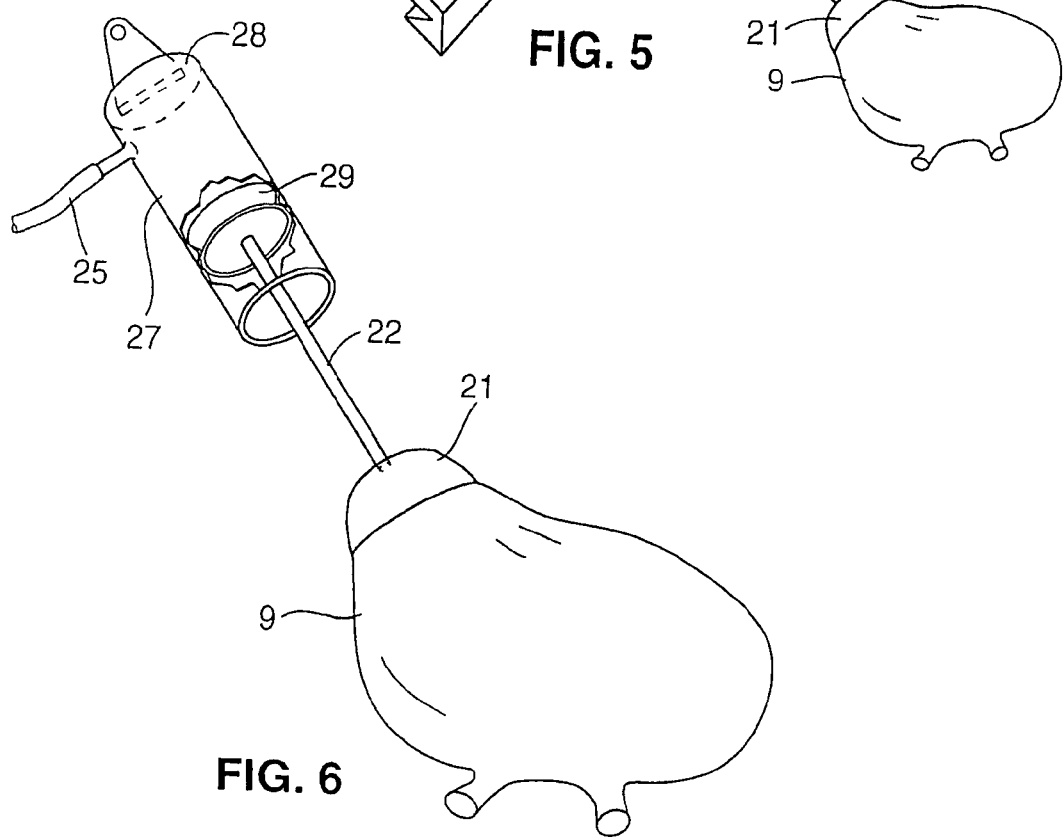
FIG. 6 is a more detailed perspective view (partially cut away to show element 29) of a portion of the FIG. 5 embodiment.

To position mount 26 in the desired position, mount 28 is translated along a sternal retractor (or operating table) until it is locked at an appropriate position, and mount 26 is loosened (relative to arm 24) so that it is free to slide along arm 24 into the desired position (thereby causing the assembly to retract heart 9 coupled to cup 21 into a desired position for surgery). In its desired position, mount 26 is tightened against arm 24 so that it thereafter remains fixed in the desired position along arm 24. Compliant element 27 includes a piston and allows tube 22 limited freedom to translate (parallel to the common axis of tube 22 and element 27) relative to arm 24, for example to accommodate motion of heart 9 as it beats during surgery. Alternatively, compliant element 27 is replaced by a spring, bellows, or other compliant element or assembly, which allows tube 22 such limited freedom to translate relative to arm 24. In the preferred embodiment shown in FIG. 6, element 27 is a tube having closed end 28, with slidable piston 29 mounted in the tube to seal the tube's other end (except that piston 29 allows air to flow from cup 21's inner surface through tube 22, piston 29, and element 27 into suction line 25). A vacuum source draws air through line 25, thus evacuating the space within element 27 between end 28 and piston 29 (except for air flowing at a low flow rate from cup 21 through tube 22 into this space). As heart 9 beats, it periodically pulls cup 21, tube 22, and piston 29 together as a unit away from end 28 of element 27, and then relaxes to allow the vacuum source to pull piston 29 back toward end 28.

The traction on heart 9 is automatic when the vacuum is engaged and cup 21 is attached to the heart. The traction and suction cup forces will remain in a fixed ratio to each other regardless of the strength of the vacuum. The ratio is determined by the area of cup 21 (over which cup 21 exerts suction) and the area of piston 29. This parameter should be controlled to ensure that the suction force is only as strong as warranted to retract the heart, in order to avoid trauma to the surface of the heart undergoing suction by the inventive apparatus. The traction force should never be strong enough to pull cup 21 off the heart (at least directly). With a vacuum accumulator of sufficient size (e.g., accumulator 7 of FIG. 1), it can be assured that the heart is returned gently to its non-retracted position even if the vacuum source is suddenly decoupled from the inventive apparatus.

Figure 5:
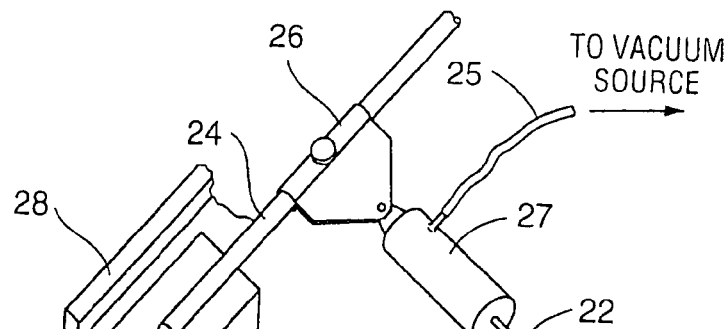
FIG. 5 is a perspective view of a portion of another preferred embodiment of the inventive organ manipulation apparatus.

In a variation on the FIG. 5 embodiment, straight rod 24 is replaced by a curved rod (whose curvature is sufficiently limited to allow mount 26 to slide along it).

Another variation on the FIG. 5 embodiment will be described with reference to FIGS. 11 and 12. In the embodiment of FIGS. 11 and 12, straight rod 24 is replaced by rigid member 54 (which is fixedly attached to mount 28), long,
threaded bolt 55 having one and mounted to member 54 (with freedom to rotate but not translate relative to member 54), and crank 57 attached to the other end of bolt 55. Bolt 55 can be rotated relative to member 54 by turning crank 57 (with non-threaded portion 55A of bolt 55 rotating in a non-threaded orifice in member 54). Mount 26 (of FIG. 5) is replaced by threaded mounting member 56 whose threads mate with those of bolt 55. Thus, threaded mounting member 56 can be advanced along bolt 55 (together with compliant element 27 and suction cup 21 attached to member 56) by turning crank 57.

Figure 7:
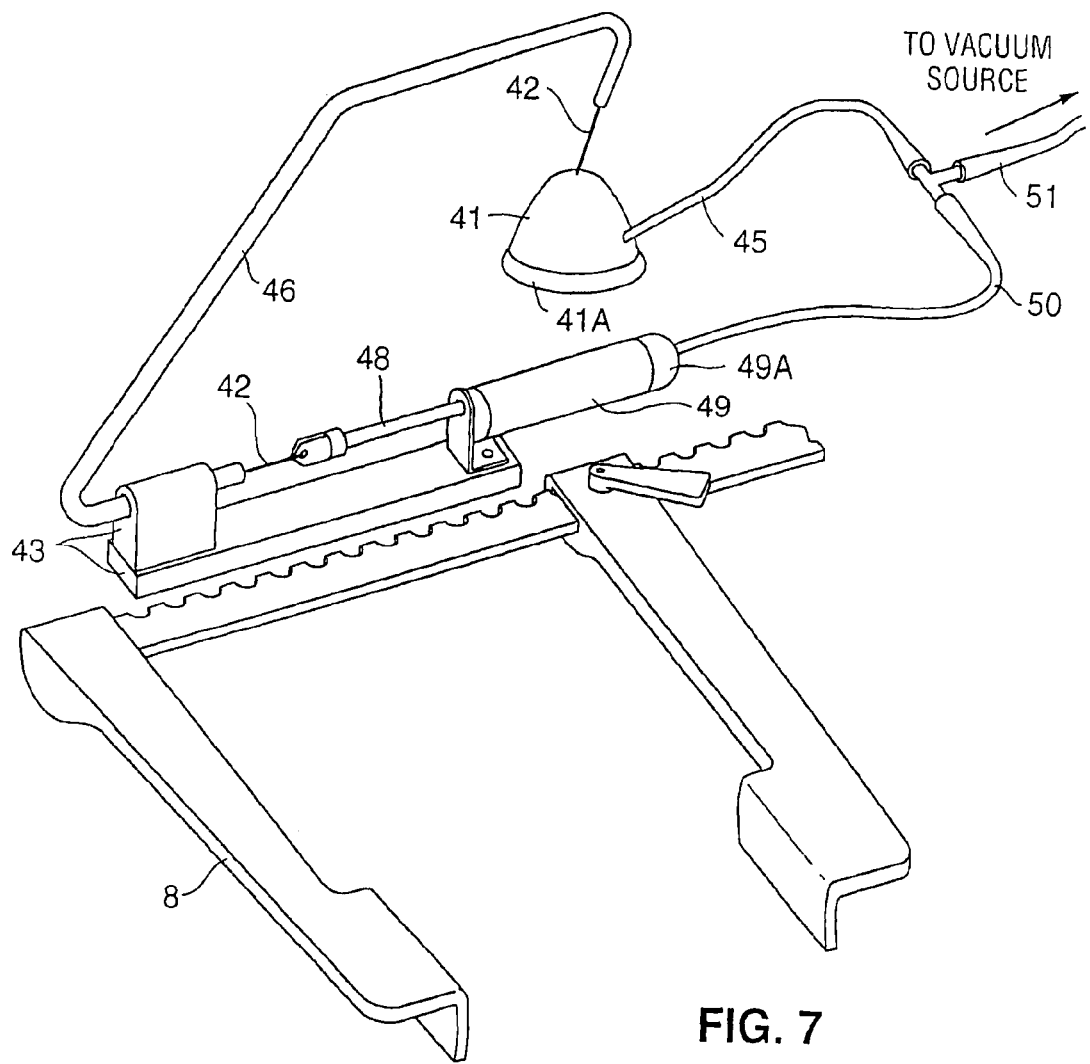
FIG. 7 is a perspective view of a portion of an alternative embodiment of the inventive organ manipulation apparatus.

In another alternative embodiment of the invention shown in FIG. 7, suction cup 41 is attached by cable 42 to hollow, flexible locking attachment arm 46 (which has both a flexible state and a rigid state). The other end of cable 42 is attached to rod 48 of piston (not shown) within compliant element 49. Mount 43 is slidably mounted relative to sternal retractor 8, arm 46 is rotatably mounted to mount 43, and chamber 49 is fixedly mounted to mount 43. After mount 43 has been moved into a desired position relative to sternal retractor 8, it can be locked to mount 43. Arm 46 can be rotated relative to mount 43 and locked into a desired rotational position relative to mount 43. Arm 46 (like arm 4 of FIG. 1) can also be moved relative to sternal retractor 8 (when in its flexible state) and then locked into a desired position by placing it in its rigid state. Thus, cup 41 can be positioned as desired relative to retractor 8. The FIG. 7 apparatus provides cup 41 freedom to swing (on cable 42) relative to arm 46 and it provides cup 41 limited freedom to move vertically relative to retractor 8.

Compliant element 49 includes a piston (not shown) which is coupled to rod 48 to allow rod 48 limited freedom to translate (parallel to the common axis of rod 48 and element 49) relative to mount 43, for example to accommodate motion of a heart (supported by cup 41) as the heart beats during surgery. In a preferred implementation, element 49 encloses a volume between closed end 49A and a slidable piston. The piston is fixedly attached to rod 48. Suction line 50 is connected to element 49 (in fluid communication with the volume enclosed by element 49) so that a vacuum source can draw air through line 50 from such enclosed volume. The same vacuum source is coupled to suction cup 41 via suction line 45. Lines 45 and 50 are both coupled by line 51 to the vacuum source. As a heart (supported by suction cup 41) beats, it periodically pulls cup 41, cable 42, rod 48, and the piston together as a unit away from end 49A of element 49, and then relaxes to allow the vacuum source to pull these components back toward end 49A. Preferably, the inner surface of arm 46 is lined with Teflon material or the like (or includes bearings made of such material) to reduce friction on cable 42.

In the FIG. 7 embodiment, suction cup 41 can be implemented to be rigid (e.g., it is composed of Delrin, ABS, Ultem, or polycarbonate plastic, or other hard plastic, with its inner surface lined with absorbent material), and has seal 41A attached (e.g., by glue, which can be Silastic Medical Adhesive Silicone Type A, available from Dow Corning, when the cup is made of Delrin plastic) around its periphery. Seal 41A can be a biocompatible foam seal as in cup 1A of FIGS. 3 and 4). Cup 41 has a shape which conforms to a target portion of a typical organ of the type to be retracted using the cup, and its inner (concave) surface is preferably smooth and lined with absorbent material to improve traction.

Adhesives suitable for use with plastic or silicone components of various embodiments of the invention include Silastic Medical Adhesive (available from Dow Corning), and Loctite 4541 or Loctite 4011 adhesive.

Figure 8:
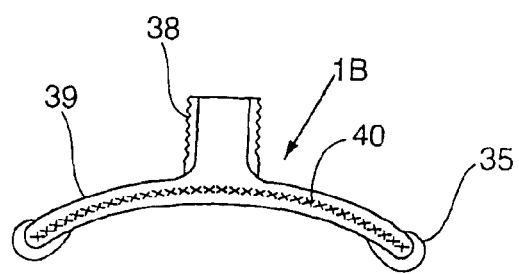
FIG. 8 is a side cross-sectional view of another preferred embodiment of the inventive suction cup.

In a class of preferred embodiments, the suction cup of the invention is implemented to be flexible but to have a shape memory. One such embodiment will next be described with reference to FIG. 8. Suction cup 1B of FIG. 8 is made of metal mesh 40 (which can resemble chicken wire) coated on both sides with a continuous sheet 39 of flexible silicone rubber (or other flexible, biocompatible material). Thus, the organ to be manipulated does not contact metal mesh 40, and instead the inner surface of the cup is a smooth sheet of silicone rubber.

Generally cylindrical attachment portion 38 defines a central orifice through the otherwise continuous sheet 39. Portion 38 is shaped for attachment to the distal end of a suction line. Tapered conformal seal 35 (preferably made of biocompatible foam) is glued to the peripheral portion of sheet 39.

In use, cup 1B of FIG. 8 is placed over the organ (with seal 35 against the organ surface) and mesh 40 is deformed (by the user's fingers) to conform with the organ surface. Mesh 40 will retain the cup in its final shape after the user has finished shaping the cup. Then, a vacuum source is coupled to the cup to draw air through the orifice through attachment portion 38. This evacuates the region bounded by the cup's inner surface, seal 35, and the organ, and causes cup 1B to exert suction on the organ.

In another class of preferred embodiments, the inventive suction cup is implemented to be rigid (e.g., it is composed of hard plastic with its inner surface lined with absorbent material), and has a seal around its periphery (e.g., a biocompatible foam seal). The cup has a shape which conforms to a target portion of a typical organ of the type to be retracted using the cup. The inner surface of the cup is preferably smooth, and lined with absorbent material to improve traction. An example of such a rigid cup is cup 41 of FIG. 7.

Figure 16:
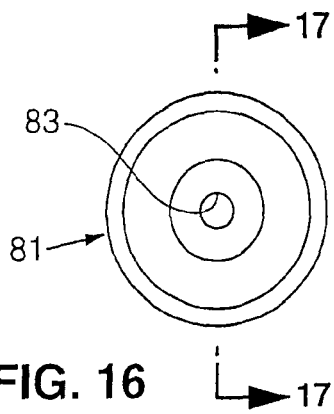
FIG. 16 is an end view of a portion of one embodiment of the inventive suction cup.
Figure 17:
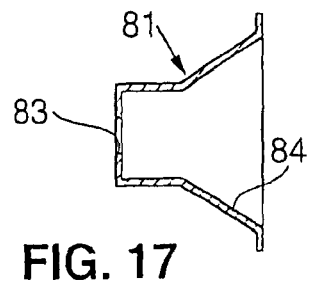
FIG. 17 is a cross-sectional view of the cup portion of FIG. 16, along line 17-17 of FIG. 16.
Figure 18:
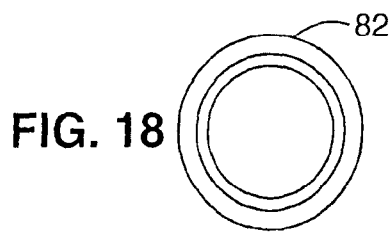
FIG. 18 is an end view of a seal for use with the cup portion of FIGS. 16 and 17.
Figure 19:
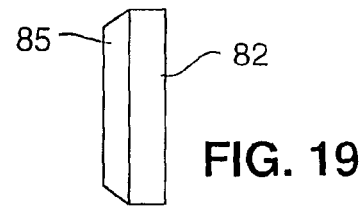
FIG. 19 is a side view of the seal of FIG. 18.

Another example is a suction cup assembled by gluing seal 82 (of FIGS. 18 and 19) to cup portion 81 (of FIGS. 16 and 17). In the embodiment of FIGS. 16-19, cup portion 81 is machined from rigid Delrin plastic, and seal 82 is made of biocompatible foam. The end surface of cup portion 81 has a central orifice 83 extending therethrough. To assemble the cup, tapered surface 85 of seal 82 is glued to tapered inner surface 84 of portion 81 at the periphery of portion 81 (e.g., with Silastic Medical Adhesive Silicone Type A, available from Dow Corning). To attach the cup to a vacuum source, a threaded pipe-shaped member is attached (e.g., using nuts and a washer) to the end surface of portion 81 (so as to extend through orifice 83), and a suction tube is then placed through the pipe-shaped member into fluid communication with inner surface 84 of portion 81. To attach the cup to a compliant joint (which is adjustably attached to a fixed structure), the pipe-shaped member can be screwed onto a threaded portion of the joint (or the pipe-shaped member can be otherwise attached to the joint). Steel wool (or another substance) can be packed loosely in the cylindrical bottom of portion 81 to prevent loss of fluid communication between the cup's inner surface 84 and the suction line, and the inner surface 84 of portion 81 can be lined with absorbent material.

Figure 20:
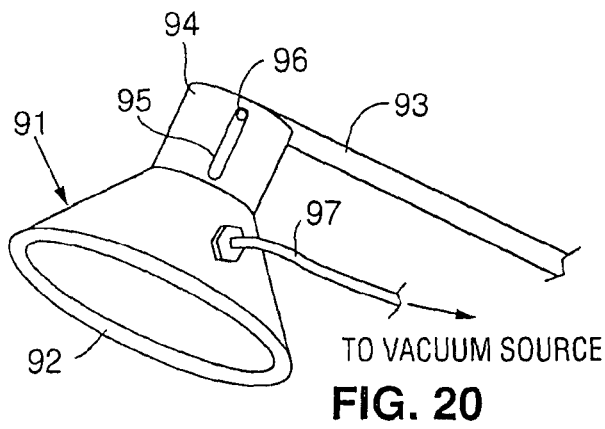
FIG. 20 is a perspective view of the suction cup and compliant joint of another alternative embodiment of the inventive apparatus.

Another embodiment of the invention will be described with reference to FIG. 20. The embodiment of FIG. 20 includes suction cup 91 (which has a circular periphery and includes seal 92 which extends around cup 91's periphery to provide a vacuum seal when the cup placed in contact with an organ), suction line 97 (which is coupled to a vacuum source to evacuate the volume inside cup 91 when the cup is positioned in contact with an organ), and a compliant joint including element 94 (having parallel slots 95 in opposing portions of its side wall) and arm 93 having pins 96 which ride in slots 95. Both slots 95 (only one of which is shown in FIG. 20) are oriented parallel to the central longitudinal axis of cup 91.

Figure 21:
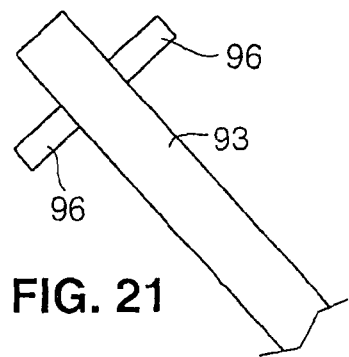
FIG. 21 is a top view of arm 93 (with pins 96) of FIG. 20.

Pins 96 and the distal portion of arm 93 are better shown in FIG. 21. With pins 96 riding in slots 95, arm 93 can support element 94, cup 91, and an organ suspended (by suction) from cup 91. Since element 94 can pivot (about pins 96) relative to arm 93, gravity will ensure that slots 95 (and the central longitudinal axis of cup 91) will remain generally vertical during organ retraction (although they will not necessarily remain fully vertical). Since slots 95 are substantially longer than the diameter of each pin 96, the assembly comprising element 94 and cup 91 is free to slide vertically relative to pins 96 during organ retraction. Thus, in response to beating of a heart suspended from cup 91, the assembly comprising element 94 and cup 91 is free to oscillate vertically relative to fixedly held pins 96 and arm 93. Cup 91 is attached to element 94 (e.g., by a binding screw) in such a manner that it can rotate freely relative to element 94. Typically, each slot 95 is sufficiently long to allow vertical oscillation of cup 91 with an amplitude up to about 0.5 inch.

Figure 22:
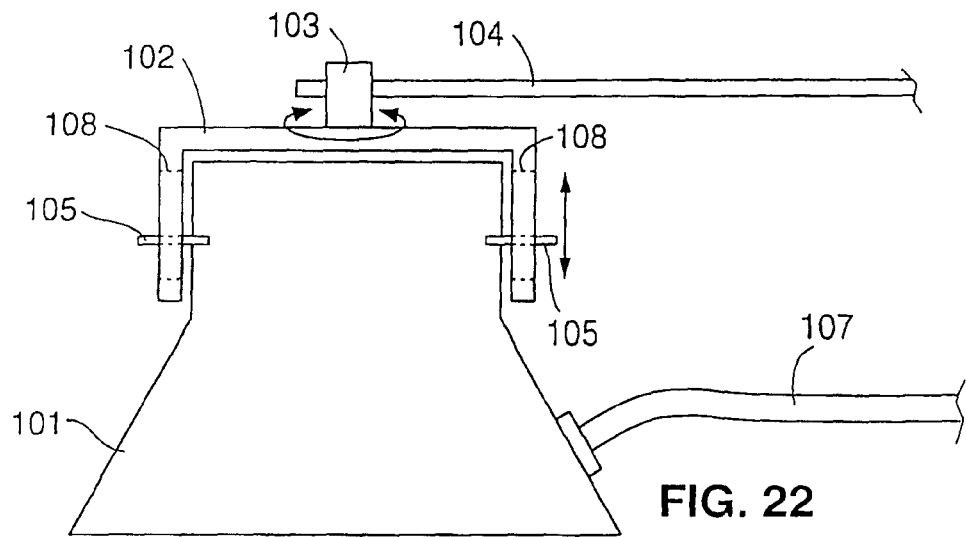
FIG. 22 is a side elevational view of the suction cup and compliant joint of another alternative embodiment of the inventive apparatus.

Another embodiment of the invention, to be described with reference to FIG. 22, is designed to minimize the overall vertical size of the suction cup and compliant joint assembly. The FIG. 22 embodiment comprises suction cup 101 (which has a circular periphery and a seal portion which extends around the periphery), suction line 107 (which is coupled to a vacuum source to evacuate the volume inside cup 101 when the cup is positioned with the seal portion in contact with an organ), and a compliant joint (including elements 102, 103, and 104) for attaching rigid arm 104 to the rest of the FIG. 22 apparatus. Two pins 105 are fixedly attached to cup 101 in the positions shown. Element 102 has parallel slots 108 in its left and right side portions, and one of the pins 105 rides in each of the slots 108. Member 103 is rotatably attached to element 102 (e.g., by a binding screw) in such a manner that element 102 is free to rotate about a vertical axis relative to member 103. Member 103 is mounted to rod 104 with freedom for member 103 to swing about the axis of rod 104. With pins 105 riding in slots 108 of member 102, arm 104 supports element 102 and member 103, and element 102 in turn supports cup 101 and an organ suspended (by suction) from cup 101. Since member 103 can pivot about arm 104 and pins 105 can rotate relative to the slots 108, gravity will ensure that the slots (and the central longitudinal axis of cup 101) will remain vertical during organ retraction. Slots 108 should be substantially longer than the diameter of each pin 105, so that pins 105 and cup 101 are free to slide vertically relative to element 102 (and thus relative to arm 104) during organ retraction. Thus, in response to beating of a heart suspended from cup 101, cup 101 is free to oscillate vertically relative to fixedly held arm 104.

Figure 23:
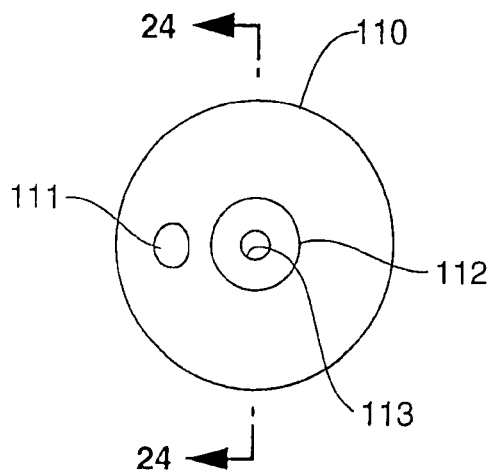
FIG. 23 is an end view of a portion of another embodiment of the inventive suction cup.
Figure 24:
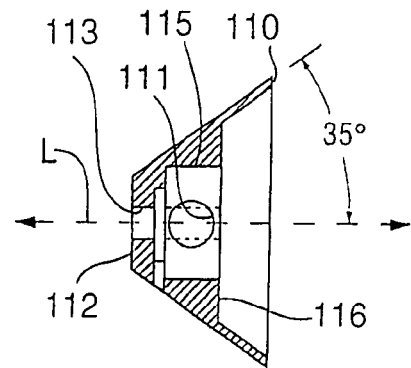
FIG. 24 is a cross-sectional view of the cup portion of FIG. 23, along line 24-24 of FIG. 23.
Figure 25:
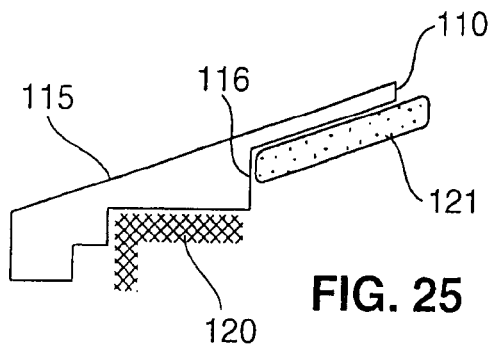
FIG. 25 is an enlarged view of a portion of the cup structure shown in FIG. 24, with gauze and a foam seal positioned in the cup.

Another example of the suction cup of the invention, designed to have low profile, will be described with reference to FIGS. 23-25. As shown in FIGS. 23 and 24, the cup has a truncated conical profile, with annular end surface 112 (having central orifice 113 extending therethrough) at one end, and circular periphery 110 at the other end. Orifice 113 is for attaching the cup to a compliant joint. Suction orifice 111 extends through the conical side wall of the cup (for connecting a suction line to the cup), and gauze can be packed into the volume surrounded by cylindrical surface 115 (FIG. 25 shows gauze 120 so packed). Foam seal 121 (partially shown in FIG. 25) can be glued to flat annular surface 116 and the conical side wall portion between surface 115 and periphery 110. The conical side wall is oriented at an angle of 35 degrees with respect to the cup's central longitudinal axis L. In a typical implementation, the cup has a height, of 0.95 inch (from end 112 to the plane of periphery 110), the center of orifice is 0.56 inch from the plane of periphery 110, the diameter of cylindrical surface 115 is 0.75 inch, and periphery 110 has a diameter of 1.95 inches. The cup of FIGS. 23 and 24 can be machined from ABS material or rigid plastic (e.g., Delrin material).

In variations on the embodiment of FIGS. 23 and 24, the angle of the conical side wall (relative to the central longitudinal axis L) is varied to vary the diameter of periphery 110. For example, this angle can be 28 degrees (rather than 35 degrees as in FIG. 24) to give periphery 110 a diameter of 1.64 inches, or 21 degrees (rather than 35 degrees) to give periphery 110 a diameter of 1.35 inches. Decreasing the angle between the conical side wall and the central longitudinal axis L decreases the diameter of periphery 110. We expect that the minimum useful diameter of periphery 110 will typically be about 1.35 inches (where the cup is to be affixed to the apex of a heart), although it may be as low as about 1 inch for some applications.

As shown in FIG. 25, when gauze 120 is packed into the volume surrounded by cylindrical surface 115 (of the cup of FIG. 24) and foam seal 121 is mounted in its proper position, there may be a gap between the seal and gauze at the right-angled intersection of surface 115 with surface 116. Under certain operating conditions, exposure of the heart tissue to such gap (during application of suction to the heart) may result in irritation to the heart tissue and/or sucking of an excessive amount of heart tissue into the cup. The FIG. 26 embodiment is designed to reduce or eliminate this potential problem. Note also that the bottom of the cup can be equipped with ribs (rib members) to prevent fabric and tissue from being sucked up into the suction tube orifice of the apparatus.

Figure 26:
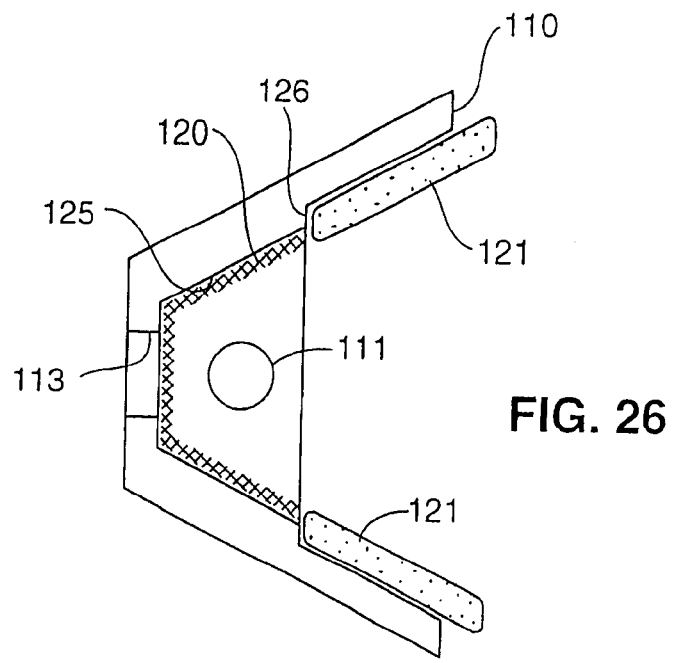
FIG. 26 is a side cross-sectional view of another embodiment of the inventive suction cup, including gauze and a foam seal positioned in the cup.

The FIG. 26 embodiment is shaped slightly differently than that of FIGS. 23-25. More specifically, the FIG. 26 embodiment differs from that of FIGS. 23-25 in that tapered (frusto-conical) surface 125 replaces cylindrical surface 115 of FIGS. 24-25, and in that flat annular surface 126 replaces surface 116. Components of the FIG. 26 embodiment that are identical to those of FIGS. 23-25 are identically numbered in FIGS. 23-26. Due to the geometry of the FIG. 26 embodiment, when gauze 120 is packed into the volume surrounded by surface 125 and foam seal 121 is mounted in its proper position, there is a smooth, continuous transition between the seal and gauze at the intersection of surface 125 with surface 126.

For heart manipulation, the inventive cup preferably has a generally hemispherical (or concave elliptical) shape with a circular (or mild elliptical) periphery, so that it conforms to the apex of the heart. Cups having less curvature (flatter cups) and/or rectangular periphery have been found to be less suitable for heart retraction since they must be affixed to relatively flatter surfaces of the heart (not to the apex) and have a greater tendency to decouple from the heart after being affixed. However, such alternative cup embodiments may be useful for retracting or otherwise manipulating organs other than the heart.

In a class of alternative embodiments, the inventive suction member is effectively custom-fitted to the organ to be supported and manipulated. One way to accomplish such custom-fitting is to implement the suction member as a pellet-filled flexible body which is impervious to fluid flow (except in that it has a gas permeable inner surface which allows a vacuum source to pull a vacuum on a portion of an organ facing the suction member). An example of such a suction member is a beanbag-like body comprising a flexible plastic enclosure filled with small pellets (which can be beads). In use, the body is placed against the appropriate part of organ and air (or other gas) within the body is then evacuated so that the pellets remaining in the evacuated body form a rigid structure which conforms to the relevant surface of the organ. Since the inner surface (which contacts the organ) of the pellet-filled body is permeable to gas, the vacuum source causes the member to exert a suction force on the organ while also maintaining the member in its rigid state.

With reference to FIG. 9, we describe in greater detail such a suction member which comprises a rigidizing bag containing pellets (which can be beads). In the FIG. 9 embodiment, the suction member comprises elastomeric beads 12 (which can be injection molding stock) contained in rigidizing bag 11. One face of bag 11 is attached by a compliant joint 13 to the distal end of rigid tube 14 (with an orifice in such face of the bag in fluid communication with the tube's interior). The proximal end of tube 14 is coupled to a vacuum source so that pulling a vacuum on tube 14 evacuates bag 11 thereby rigidizing it. The inner surface of bag 11 is permeable to gas (e.g., it is porous or has at least one small orifice extending through it) so that the vacuum source will also cause the suction member to exert suction on an organ in contact with the member's inner surface.

In a variation on the FIG. 9 embodiment, only the perimeter of the suction member is rigidizible (to conform with an organ surface against which the member is placed). The member's central portion is rigid. For example, as shown in FIG. 10, the suction member comprises a rigid central portion 18 (having concave inner surface, and preferably made of hard plastic lined with soft absorbent fabric or other absorbent material) and a rigidizing bag 19 (containing elastomeric beads) which extends around the periphery of central portion 18. Compliant joint 13 is coupled between the distal end of rigid tube 14 and central portion 18. The interior of tube 14 is in fluid communication with the interior of bag 19, so that pulling a vacuum on tube 14 evacuates bag 19 thereby rigidizing it. The inner surface of portion 18 (or bag 19) is permeable to gas (e.g., it is porous or has at least one small orifice extending through it to tube 14) so that the vacuum source will also cause the suction member to exert suction on an organ in contact with the member's inner surface.

In preferred embodiments (including the FIG. 1 and FIG. 2 embodiments), the suction member of the inventive apparatus is implemented with a smooth inner surface (e.g., a smooth biocompatible foam seal around the periphery and a smooth fabric surface between the center and periphery) to provide traction (e.g., by absorbing blood which would otherwise cause the member to slip from the organ) while avoiding trauma to the organ (e.g., bruising) during retraction. For many surgical applications, it is important to implement the suction member with such a smooth inner surface. Alternatively, in some surgical applications in which the organ to be manipulated is not highly vulnerable to trauma, it may be desirable for the inner surface of the suction member to be somewhat rough (e.g., with bumps or the like protruding therefrom) or textured to improve traction between the suction member and organ.

The suction member of the invention (e.g., suction cup 61 shown in FIG. 13) can be made of flexible plastic film (e.g., film 62 of cup 61) with its inner surface lined with absorbent material (e.g., felt or felt-like material), and with a hyperextensible elastomeric seal (e.g., seal 63 of cup 61) around its periphery. The absorbent material should not intrude between the organ and the elastomeric seal, so that a good fluid seal can be maintained by direct contact of the elastomer with the organ.

The suction member of the invention can be connected to a constant force spring arrangement which applies a constant retraction force to the suction member, while still providing rotational and translational compliance. For example, in the FIG. 13 embodiment, suction cup 61 is attached to the distal end of cable 64. Support assembly 65 includes low tension, constant force spring 66. The proximal end of cable 64 is attached to spring 66. Support assembly 65 is designed to be adjustably mounted (preferably with a low profile) to a sternal retractor or other fixed structure. Assembly 65 and cable 64 support cup 61 (and the organ held by suction to cup 61) with a constant force, while allowing cup 61 freedom to swing and rotate relative to assembly 65 and to undergo vertical oscillation relative to assembly 65 (e.g., in response to beating motion of a beating heart).

A constant force spring arrangement which applies a constant retraction force to a suction cup can also be used in a variation on the above-described FIG. 1 embodiment. In this variation, the constant force spring arrangement is coupled between suction cup 1 and the distal end of portion 4B of attachment arm 4 (in place of sliding ball joint 3). The spring is configured to apply a constant retraction force to suction cup 1, while still providing rotational and translational compliance by allowing the cup to rotate relative to arm 4 and to undergo vertical oscillation relative to arm 4.

In other variations, a set of one or more springs is employed to apply a retraction force (which can but need not be a constant force) to the suction cup of FIG. 1 or any of the other embodiments of the invention. In one such variation, the set of springs is coupled between the suction cup (e.g., cup 1) and the distal end of the arm which supports it (e.g., attachment arm 4). The set of springs allows the cup to vertical oscillation relative to arm 4. Preferably, the set of springs is rotatably mounted to the cup (e.g., by being attached between the support arm and a plate, where the plate is rotatably mounted to the cup) so that the cup is free to rotate about a vertical axis relative to the support arm, as well as to undergo vertical oscillation relative to the support arm.

In other embodiments, the compliant joint of the invention is implemented as a universal joint, or a set of two or more universal joints.

An aspect of the invention is a preferred method for retracting a beating heart in which a suction member (implemented in accordance with any embodiment of the inventive apparatus) is affixed to a heart at position concentric with the apex of the heart. Preferably the suction member has sufficient curvature to conform with the apex and is shaped to be at least generally symmetric with the apex. Suction is applied to the heart by coupling the suction member to a vacuum source, and the suction member is moved to retract the heart to a desired position for surgery. Preferably, the suction member is mounted to a fixed assembly (e.g., a fixedly mounted sternal retractor) by a compliant joint so that the suction member does not constrain normal beating motion of the heart during gross movement of the suction member and heart into the desired position, and while the suction member supports the heart (e.g., while the heart is suspended vertically below the member) in such position. In such preferred embodiments, the suction member has an axis of symmetry, and as the heart beats, the heart is free to expand and contract, with the compliant joint allowing the suction member to oscillate along the axis of the suction member (e.g., along a vertical axis) and to twist about the axis (e.g., the vertical axis) relative to the fixed assembly, so that hemodynamic function is not compromised.

Another aspect of the invention is a method including the steps of:

1. placing a suction cup on the apex of the heart, and applying suction to hold the heart;

2. adjusting an arm (e.g., arm 4 of FIG. 1 or arm 10 of FIG. 2) which supports the suction cup (e.g., by sliding arm 10 relative to holder 11, and/or sliding holder 11 relative to element 8) to achieve the desired amount of retraction;

3. adjusting the arm (which supports the suction cup) to achieve an angle between such arm and the suction cup which allows maximal suction cup displacement (relative to the arm) to occur with each heart beat; and 4. then, performing surgery on the heart while it is suspended (via suction) from the cup.

The inventive method and apparatus allows manipulation of a beating human heart so as to expose lateral or posterior coronary arteries for the purpose of bypassing those vessels.

Since the inventive apparatus does not rigidly constrain the heart muscle, the invention allows the heart anatomy to retain its natural shape and performance. The compliance provided by the apparatus is intended to replicate the motion allowed when the heart is manipulated either directly by the human hand or by pulling the pericardium. Overall, there are at least three attributes of the inventive apparatus which make it a superior organ manipulator with regard to hemodynamics and overall access and stabilization. These attributes and the corresponding benefits are summarized in Table 1:

TABLE 1

| Attribute | Benefit |
| --- | --- |
| Built in system compliance | Less strain on hemodynamic performance because the heart can beat normally both during movement and while being supported in the final manipulated position; Less force is required to hold the heart because the apparatus is not working against the heartbeat; Attachment with compliance can be achieved in a wide variety of different positions of the heart (or other organ). |
| The apparatus pulls rather than pushes the organ to manipulate the organ | Chambers and vessels of the heart are not compressed, allowing them to more closely maintain their natural shape and fill volumes; Ventricles are placed in tension, creating pre-load for contractility. |
| Separation of gross and local stabilization | With separate gross stabilization (achieved by the inventive apparatus) with ventricles in tension, less local anastomotic stabilization force (to be provided by a device other than the inventive apparatus) is needed, reducing deflection of the heart chamber inwards (such inward deflection undesirably leads to reduced filling); Ease of use; Improved reliability. |

Although preferred embodiments of the invention are methods and apparatus for cardiac retraction during beating heart surgery, other embodiments are methods and apparatus for retracting almost all other internal organs. The size, shape, and material of the suction cup employed as well as the amount of vacuum applied can be varied to match the topology and consistency of the organ tissue. More than one suction cup at a time can be applied to each organ, to provide greater or more stable manipulation. Multiple cups can be mounted to a single support structure (with one or more compliant joints providing compliance between each cup and the support structure), and the cups can then be affixed to the organ in such a way as to retract the organ in a desired direction without interfering with the natural movement of the organ. Affixing of multiple suction cups to an organ would allow torsion to be applied to the organ. Organs often must be twisted or rotated for better tissue presentation preliminary to surgery.

Other alternative embodiments of the invention include multiple suction cups mounted at the ends of fingers, with the fingers being configured to fan out and then move together to grip the heart or other organ with non-slip surfaces. The fingers are mounted on a compliant joint which is in turn supported by a fixed structure (or the fingers themselves have compliance and function as a compliant joint), so that the fingers do not constrain normal beating motion of the heart (or normal motion of the other organ) during gross movement of the fingers and organ into the desired position or during surgery on the organ held by the fingers.

An example of this class of embodiments will be described with reference to FIGS. 14 and 15. In the FIG. 14 embodiment, finger assembly 71 includes three suction cups 75 and three hinged fingers 72. Each cup 75 is mounted at the distal end of one of the fingers. Each finger 72 has a hinge 73 (which is coupled to extension member 76) and another hinge 73A, and member 76 is adjustably coupled to a sternal retractor (not shown) or other fixed structure. Extension member 76 is coupled to hinges 73 in such a manner that a user can manipulate member 76 to cause hinges 73 to spread fingers 72 (before assembly 71 grips a beating heart or other organ) and then to cause hinges 73 to gather fingers 72 until cups 75 grip the organ (as shown in FIG. 14). Then, a vacuum source coupled to cups 75 (via suction lines extending through fingers 72 and member 76) is actuated to provide suction force on the organ. Member 76 can then be moved to retract the organ into a desired position for surgery.

Assembly 71 functions as a compliant joint, in addition to functioning as a set of suction cups, since while assembly 71 grips the organ, hinges 73 and 73A allow fingers 72 to flex in response to normal movement of the organ (e.g., in response to beating movement of a beating heart). For example, as shown in FIG. 15, when the surface of heart 9 moves upward (from the lower position shown in phantom view) to the raised position shown by the solid line, hinges 73 and 73A pivot to allow finger 72 to move (from the relatively more flexed position shown in phantom view) to the relatively less flexed position shown by the solid lines. This compliance provided by the flexing action of fingers 72 allows cups 72 to oscillate in parallel to the axis of member 76 as the heart beats. Preferably, fingers 72 are coupled to extension member 76 in such a manner that assembly 71 has freedom also to rotate about the axis of member 76 (while member 76 remains fixed).

Other examples of embodiments including finger assemblies are variations (on any of the "single suction cup" embodiments described herein which include a single suction cup) in which a retracting finger assembly replaces the single suction cup. In variations on such embodiments, the retracting finger assembly does not include a suction cup at the end of each finger, and instead each finger has a non-slip surface at its distal end so that an organ (e.g., a beating heart) can be gripped by the non-slip surfaces.

Figure 28:
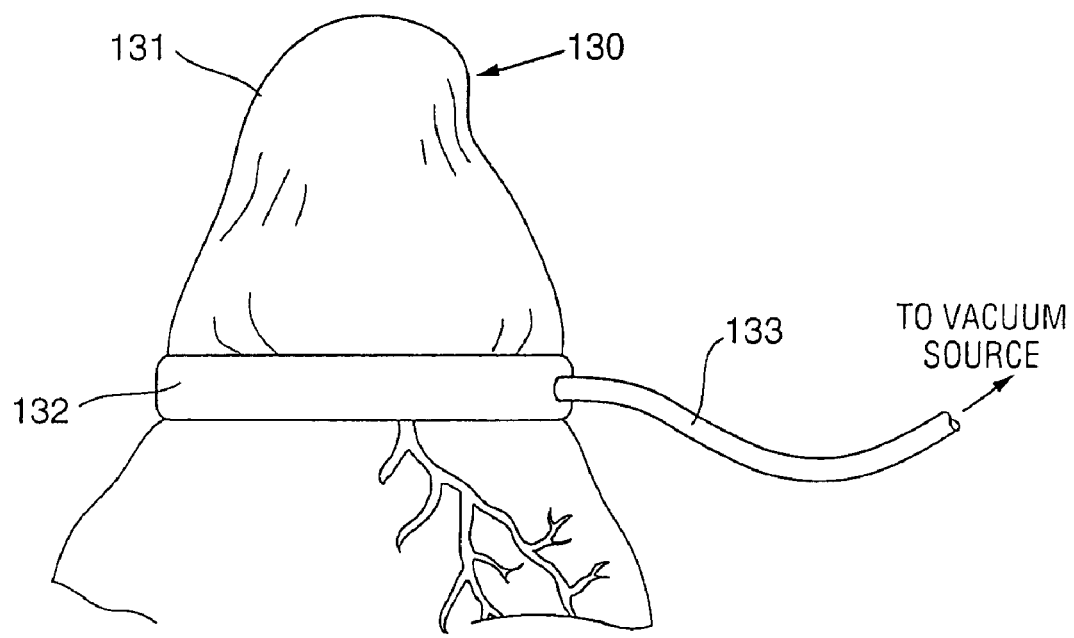
FIG. 28 is a perspective view of another embodiment of the inventive suction member.

FIG. 28 is a perspective view of another embodiment of the inventive suction member, which is a variation on suction cup 61 of FIG. 13. Suction member 130 of FIG. 28 comprises flexible bag-like membrane 131 (which can be made of plastic film and preferably has its inner surface lined with absorbent material), and ring 132 around the periphery of membrane 131. Ring 132 is preferably made of plastic or silicone, and its inner face supports sealing material (e.g., elastomeric material) which faces the heart and is capable of forming a seal around the periphery of member 130. The absorbent material which lines membrane 131 should not intrude between the heart (being held or moved by suction) and the sealing surface of ring 132, so that a good fluid seal can be maintained by direct contact of the sealing material with the organ. Suction line 133 is coupled to ring 132, with its distal end sealed around an orifice extending through ring 132 so as to be in fluid communication with the inner surface of membrane 131.

Figure 29:
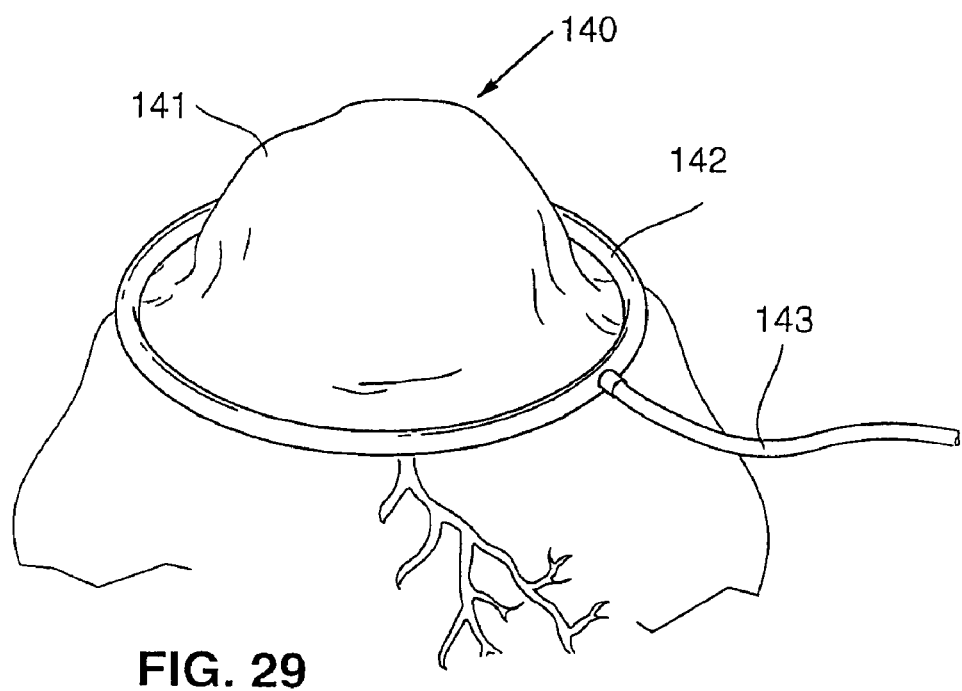
FIG. 29 is a perspective view of another embodiment of the inventive suction member.

The suction member of FIG. 29 is a variation on that of FIG. 28. Suction member 140 of FIG. 29 comprises flexible bag-like membrane 141 (which can be made of plastic film and preferably has its inner surface lined with absorbent material), and ring 142 around the periphery of membrane 141. Ring 142 (which is narrower than relatively wide ring 132) is preferably made of plastic or silicone, and its inner face supports sealing material which faces the heart and is capable of forming a seal around the periphery of member 140. Suction line 143 is coupled to ring 142, with its distal end sealed around an orifice extending through ring 142 so as to be in fluid communication with the inner surface of membrane 141.

The design of the FIG. 13, FIG. 28, and FIG. 29 embodiments of the invention (including a flexible film or membrane with a seal around its periphery) has several advantages including the following: the design helps maintain the natural shape of the beating heart at all times to maintain hemodynamic function; and placement of the suction member at any of various places on the heart (e.g., on the apex, right ventricle, or AV groove) does not detract from or interfere with the mechanical or electrical function of the beating heart.

Figure 30:
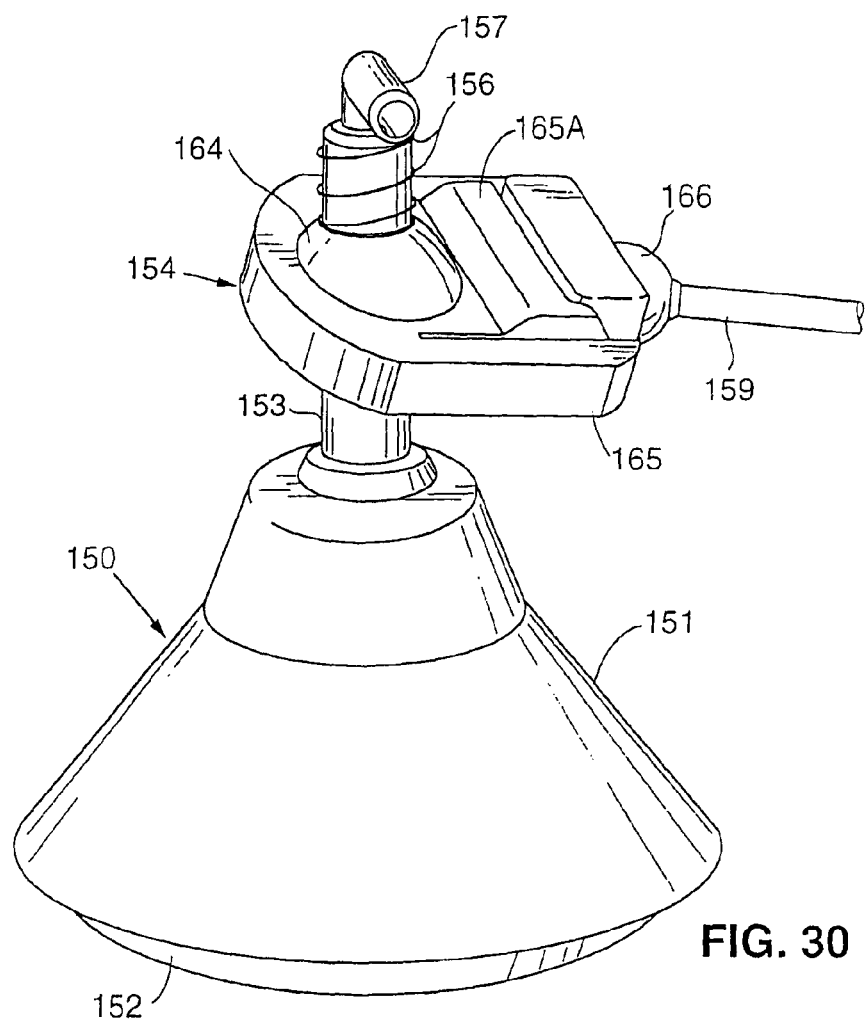
FIG. 30 is a perspective view of another embodiment of the inventive suction member, with a compliant joint for mounting it to a rigid structure.

FIG. 30 is a perspective view of another embodiment of the inventive suction member, with a compliant joint for mounting it to a rigid structure. Suction member 150 of FIG. 30 includes a cup 151, a hollow shaft 153 fixedly attached to cup 151, and fitting 157 (for attaching a suction line to shaft 153). Shaft 153 is oriented with its axis parallel to the central longitudinal axis of cup 151. Conforming seal 152 (which performs the same function as does above-described seal 35) is mounted to the distal surface of cup 151. Seal 175 forms a seal with the heart (or other organ) while preventing the organ tissue from being sucked substantially into the internal area of cup 151. The concave inner surface of cup 151 (not shown in FIG. 30) is preferably lined with soft and absorbent material (preferably non-woven rayon or viscose fabric, but alternatively another material such as gauze or a material of a type currently used in neuro-sponges). The absorbent material is preferably capable of absorbing enough blood and/or other bodily fluid to significantly improve traction between the cup and organ, and preferably also functions to diffuse the suction exerted by member 150 on the organ.

Conforming seal 152 is preferably made of biocompatible foam having open cells (to allow slow flow of air through seal 152), except in that is has closed cells (which define a "skin") on the distal surface of seal 152 (the surface designed to contact the organ).

Still with reference to FIG. 30, compliant joint 154 attached to the distal end of arm 159 comprises ball 164, socket member 165, and ball connector 166. Connector 166 is fixedly attached to the distal end of arm 159. Arm 159 (which can be a locking attachment arm having a flexible state as well a rigid state) has a distal end which is fixedly mounted to a rigid structure (e.g., a sternal retractor). Socket member 165 is attached to connector 166 with freedom to rotate relative to connector 166 about the axis of the distal portion of arm 159. Ball 164 is attached to member 165 with freedom to rotate relative to member 165. Ball 164 defines a central channel, and shaft 153 of suction member 150 extends through this channel (as shown).

Preferably, spring 156 is positioned around shaft 153 between fitting 157 and ball 164. Preferably, spring 156 is compressed by the force exerted on it by fitting 157 and ball 164, and spring 156 (assuming axial compression of the spring in the range 0.1 inch to 0.5 inch during use) has a spring constant (k) in the range from k=2.5 to k=5.0, inclusive (k 3.8 would be typical). Optionally, spring 156 is omitted.

During beating heart surgery, the FIG. 30 assembly functions as follows. Cup 150 (including shaft 153) is fixedly attached by suction (exerted through fitting 157) to the surface of the beating heart, and thus moves as a unit with the beating heart. The weight of the heart causes shaft 153 (and the entire cup 150) and ball 164 to rotate as a unit (relative to member 165) so that shaft 153 is oriented vertically. As shaft 153 and ball 164 rotate as described relative to member 165, member 165 typically also rotates relative to fixed ball connector 166. In some implementations, the device is implemented so that rotation of member 165 relative to connector 166 occurs only during gross manipulation of the suction member (with the heart coupled by suction to the suction member). As the vertically oriented shaft 153 oscillates vertically as a unit with the surface of the beating heart, shaft 153 slides (through ball 164's central channel) relative to ball 164 (while the vertical position of ball 164 is fixed by socket member 165.

Spring 156 damps the oscillating motion of shaft 153 relative to ball 164, in the following manner. As shaft 153 slides vertically downward relative to ball 164, spring 156 is compressed (converting some of the kinetic energy of shaft 153 into potential energy). Then, as shaft 153 slides vertically upward relative to ball 164, spring 156 relaxes (elongates) back to its equilibrium position (assisting in pulling the heart surface upward as some of the potential energy stored in the spring is converted to kinetic energy of shaft 153).

Preferably, socket member 165 includes a pivoting latch 165A which can be manually rotated between two positions: a first position (shown in FIG. 30) in which it does not prevent shaft 153 from translating relative to ball 164; and a second (locking) position in which it prevents translation of shaft 153 relative to ball 164. The pivot about which latch 165A rotates is attached to member 165, and thus latch 165A is fixed relative to arm 159 except in that it is free to rotate (as a unit with member 165) about the axis of arm 159's distal end. When latch 165A is rotated into the locking position, its free end hooks onto (or is wedged against) fitting 157 so as to prevent translation of shaft 153 relative to ball 164.

It is contemplated that surgeons will find it useful from time to time (during beating heart surgery) to move a latch (e.g., latch 165A) temporarily into a locking position to constrain heart movement temporarily, such as if the surgeon is having difficulty in executing a graft.

Alternative embodiments of the invention include a latch (or other simple locking structure) other than latch 165A. Each such locking structure can be moved between two positions: a first position in which it allows shaft 153 freedom to translate relative to ball 164 (or more generally, in which it allows the suction member freedom to translate along the suction member's central axis relative to the fixed structure to which the suction member is mounted); and a second (locking) position in which it prevents relative motion of shaft 153 relative to bail 164 (or more generally, in which it prevents relative motion of the suction member relative to the fixed structure to which the suction member is mounted). In some such embodiments, a latch (in its locking position) extends between socket member 165 (or an alternative socket member implementation) and fitting 157. In other such embodiments, the latch (in its locking position) extends between member 165 (or an alternative socket member implementation) and cup 151.

Figure 31:
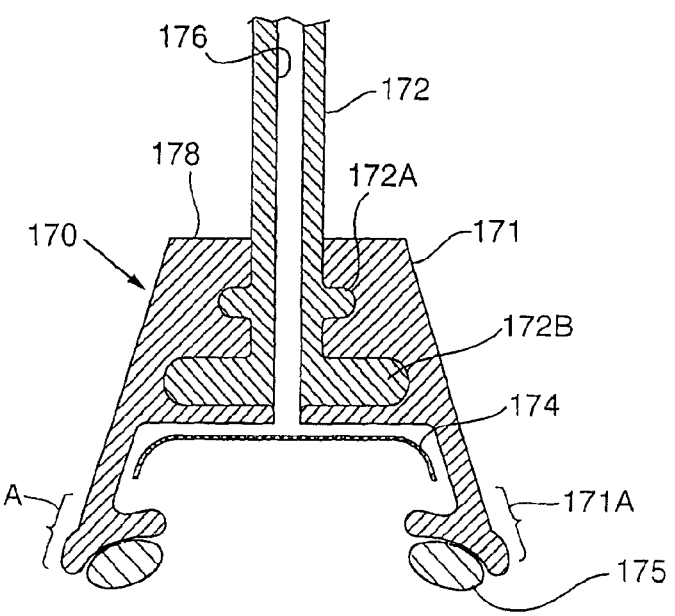
FIG. 31 is a side cross-sectional view of another embodiment of the inventive suction member.

FIG. 31 is a cross-sectional view of another embodiment of the inventive suction member. Suction member 170 of FIG. 31 has a cup portion comprising a rigid core 172 (preferably made of rigid plastic) and a flexible cup 171 (preferably made of silicone molded over core 172). Rigid core 172 has a shaft portion through which orifice 176 extends, and projections 172A and 172B which extend radially out from the shaft portion. The shaft portion of core 172 is to be mounted through ball 164 of compliant joint 154 (or to another embodiment of the compliant joint of the invention), and a vacuum fitting (e.g., fitting 157 of FIG. 30) is typically mounted at the upper end of the shaft (so that cup 170 is free to translate relative to the ball of the compliant joint, with the constraint that the ball stops the vacuum fitting at one end of the cup's range of motion and the ball stops upper surface 178 of cup 170 at the other end of the cup's range of motion).

Silicone cup 171 can be molded over core 172 (which can but need not be formed of plastic), so that core 172 provides axial support for cup 171 and so that the shaft portion of core 172 can be attached to a compliant joint (thereby attaching cup 171 to the compliant joint without interfering with the function of flexible flange portion 171A of cup 171). Conforming seal 175 (which performs the same function as does above-described seal 35) is mounted to the distal surface of flange 171A. Flange portion 171A of cup 171 provides compliance, allowing seal 175 to move in the axial direction (the vertical direction in FIG. 31) and lateral directions (perpendicular to the axial direction) relative to the surface of the heart (or other organ), so that seal 175 can conform to organ surfaces having any of a wide range of sizes and shapes. Seal 175 conforms to and forms a seal with the heart (or other organ) while preventing the organ tissue from being sucked substantially into the internal area of the cup. The concave inner surface of cup 171 is preferably lined with soft and absorbent material 174. Material 174 is preferably non-woven rayon or viscose fabric, but can alternatively be another material (such as material of a type currently used in neurosponges). Material 174 is preferably capable of absorbing enough blood and/or other bodily fluid to significantly improve traction between the cup and organ, and preferably also functions to diffuse the suction exerted by member 170 on the organ.

Conforming seal 175 is preferably made of biocompatible foam having open cells (to allow slow flow of air through seal 175), except in that it has closed cells (which define a "skin") on the distal surface of seal 175 (the surface designed to contact the organ).

In typical implementations of suction member 170 of FIG. 31, the surface area which faces the organ is in the range 0.6-1.5 inch$^2$, the vacuum provided by the vacuum source (via orifice 176) is in the range −65 mm Hg to −400 mm Hg (preferably −250 mm Hg to −350 mm Hg. In preferred implementation, the vacuum provided by the vacuum source is equal (or substantially equal) to −300 mm Hg.

A preferred implementation of flexible locking attachment arm 4 of FIG. 1 (or arm 159 of FIG. 30) will be described with reference to FIGS. 32 and 33. The arm of FIG. 32 includes a distal joint 202, a number of ball joints 203, a housing 205 (whose distal surface abuts the ball joint 203 farthest from joint 202), and a flexible cable 200 strung through elements 202, 203, and 205. Cable 200 has cylinder 201 fixedly attached at its distal end. A conventional cable length control mechanism, comprising housing 205, knob 204, pin 206, and a bar clamp assembly which comprises base 207, foot 208, lever 209, and cam 210 (between lever 209 and foot 208), is employed to control the amount of slack in cable 200 between distal joint 202 and the distal end of housing 205. When the clamp assembly and knob 204 are manipulated to introduce slack in cable 200, the ball joints 203 have freedom to slide and rotate relative to each other (and thus the arm has freedom to bend into a desired configuration). When ball joints 203 have moved into relative positions which give the arm its desired configuration, the clamp assembly and knob 204 are again manipulated to shorten the length of cable 200 between joint 202 and the distal end of housing 205. Such shortening of the effective length of the cable causes ball 200 to move joint 202 toward housing 205, thereby squeezing ball joints 203 between joint 202 and housing 205 so as to fix the ball joints 203 in their desired relative positions (which in turn keeps the arm fixed in a rigid state having the desired configuration).

It should be understood that the term "cable" is used herein (to describe an element of a flexible locking arm) in a general sense denoting flexible metal cables and wires as well as other flexible elongated elements capable of being given greater or lesser amounts of slack to change the arm between rigid and flexible states.

Figure 32:
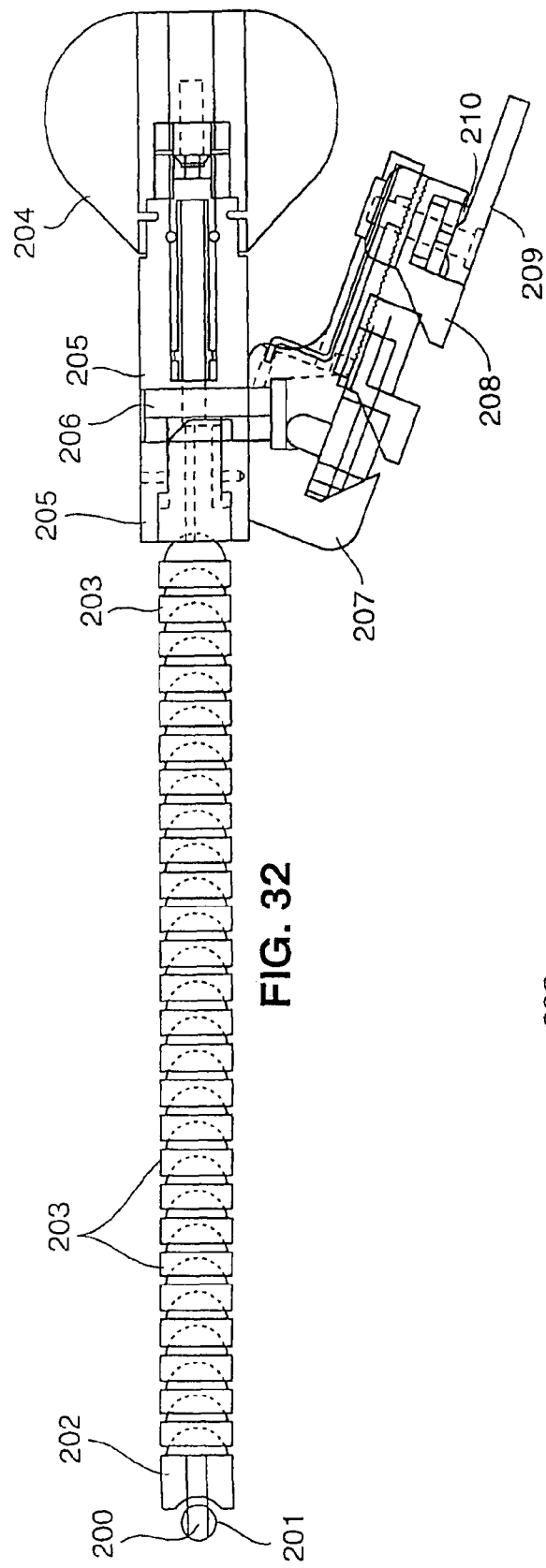
FIG. 32 is a side elevational view of a preferred flexible locking attachment arm for use in supporting the suction member and compliant joint of the invention.
Figure 33:
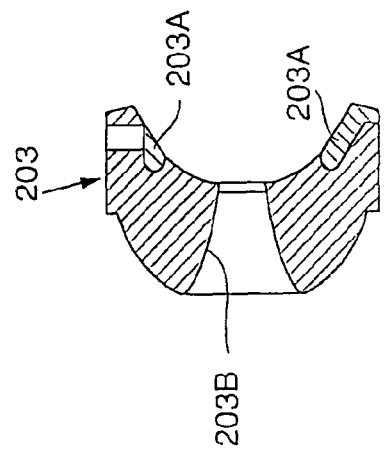
FIG. 33 is a side cross-sectional view of one ball joint of the arm of FIG. 32.

Conventional ball joints (suitable for use as ball joints 203 in FIG. 32) are made of stainless steel, and have roughly the same shape as ball joint 203 shown in FIG. 33. This shape includes a convex "ball" surface (at the left side of FIG. 33) and a concave "socket" surface (at the right side of FIG. 33). The socket surface of each ball joint is pressed against the ball surface of the ball joint immediately distal thereto, when the ball joints are tightened together to put the arm in its rigid state. However, the shape of conventional ball joints does not provide good mechanical advantage when the ball joints are tightened together to put the arm in the rigid state. Further, the surface composition (and smooth texture) of conventional ball joints provides very little friction to assist with locking the arm when the ball joints are tightened together.

One aspect of the present invention is an improved ball joint design which reduces or eliminates the noted disadvantages and limitations of conventional ball joints. Ball joint 203 of FIG. 33 embodies this improved design. Ball joint 203 of FIG. 33 has shortened length and increased diameter relative to conventional ball joints. Preferably, ball joint 203's diameter (from top to bottom in FIG. 33) is greater than ball joint 203's length (from left to right in FIG. 33). For example, the length is 0.345 inch and the diameter is 0.460 inch in a preferred embodiment (or more generally, the ratio of the length to the diameter is at least substantially equal to 0.345/0.460). The shape of the socket surface is modified (to be as shown in FIG. 33) to provide increased contact area between abutting ball and socket surfaces of adjacent ball joints which are tightened together. Central hole 203B through each ball joint is angled (or tapered) to allow the cable to pass through it smoothly and easily (and to improve rigidity in the rigid state, since cable length with the improved ball joint design will not change as much as with the conventional ball joint design during each transition from the flexible to the rigid state).

Also, two materials are used in manufacturing the improved ball joint 203. The main portion of the ball joint is molded from hard plastic, such as polycarbonate plastic, Ultem (polyetherimide) plastic, or SST material. Then, a portion 203A of the socket surface is coated with material having greater friction (such as a thermoplastic or silicone elastomer). This coating of portion 203A can be accomplished by injection molding the thermoplastic or silicone elastomer into a groove (at the location of portion 203A) in the socket surface of the hard plastic molding. Preferably, portion 203A is an annular (O-ring shaped) region comprising thermoplastic or silicone elastomer material having Shore A durometer in the range 50 to 90. Alternatively, most or all of the socket surface of the ball joint is coated with thermoplastic or silicone elastomer (or other relatively high friction material). Also alternatively, all or part of the socket surface of each ball joint (i.e., the part of each concave socket which mates with an adjacent convex ball surface) is molded with a rough texture which provides sufficiently high friction to adequately lock the arm when a convex ball surface of an adjacent ball joint is tightened against the portion having rough texture. An example of the latter embodiment is a variation on ball joint 203 of FIG. 33 which is molded from hard plastic with a smooth (non-textured) outer surface, except that portion 203A of its concave socket surface is molded with a rough texture.

In some embodiments, adjacent pairs of the ball joints 203 are made from materials having different hardness (so that the harder material wedges into the softer material). In one such embodiment (in which it is assumed that the ball joint at the distal end is the "first" ball joint, and the other ball joints are consecutively numbered according to increasingly proximal position), the even (or odd) ball joints are molded from polycarbonate plastic, and the odd (even) ball joints are molded from Ultem plastic.

Figure 34:
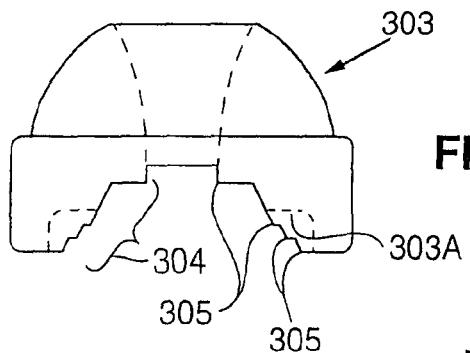
FIG. 34 is a side cross-sectional view of ball joint of another embodiment of a flexible locking attachment arm for use in supporting the suction member and compliant joint of the invention.

In a variation on the FIG. 32 embodiment of the inventive flexible locking attachment arm, ball joint 303 of FIG. 34 replaces each ball joint 203 of FIG. 32. Ball joint 303 differs from ball joint 203 in that socket surface 304 of ball joint 303 has a jagged profile, comprising circular shoulders 305. Shoulders 305 are designed to bite into the convex ball surface of the adjacent ball joint 303, thus increasing friction between the convex ball surface and the socket surface 304 in contact therewith, to assist with locking the arm when the ball joints are tightened together. Annular (O-ring shaped) portion 303A of ball joint 303 is optionally made of material which (when in contact with the convex ball surface of an adjacent ball joint) provides greater friction than if portion 303A were made of the same hard plastic material (e.g., polycarbonate or Ultem plastic, or SST material) as is the rest of ball joint 303. In preferred embodiments, region 303A comprises thermoplastic or silicone elastomer material having Shore A durometer in the range 50 to 90 (which is molded into a recess in the remaining portion of ball joint 303).

Figure 35:
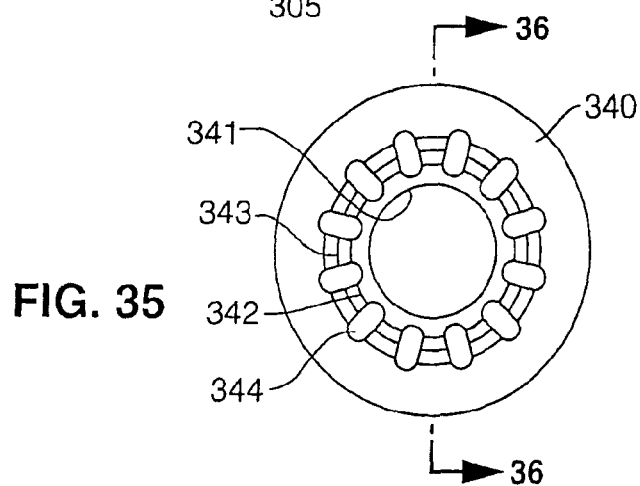
FIG. 35 is a top elevational view of a sleeve of another embodiment of a flexible locking attachment arm for use in supporting the suction member and compliant joint of the invention.
Figure 36:
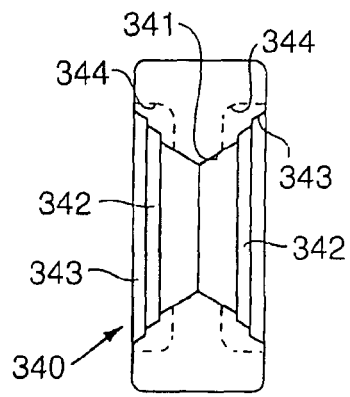
Figure 37:
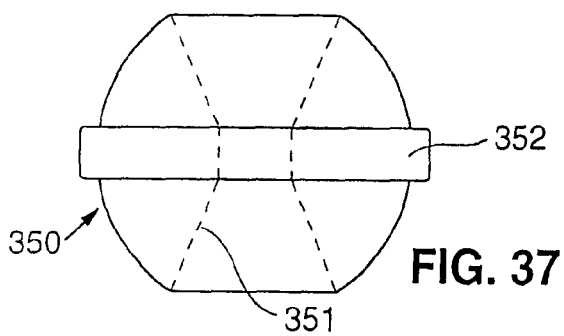
FIG. 37 is a side elevational view of a ball joint for use with the sleeve of FIG. 35 in a flexible locking attachment arm.
Figure 38:
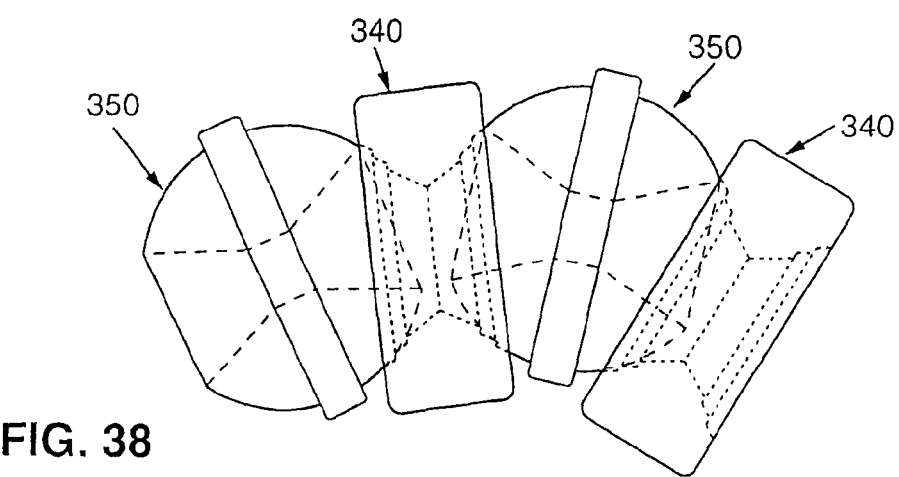
FIG. 38 is a side elevational view of a portion of a flexible locking attachment arm including alternating ball joints (of the type shown in FIG. 37) and sleeves (of the type shown in FIG. 35).

In another variation on the FIG. 32 embodiment of the inventive flexible locking attachment arm (of which a portion is shown in FIG. 38), alternating ball joints 350 (shown in FIG. 37) and sleeves 340 (shown in FIGS. 35 and 36) replace ball joints 203. FIG. 35 is a top elevational view of sleeve 340, FIG. 36 is a cross-sectional view of sleeve 340 taken along line 36-36 of FIG. 35, and FIG. 37 is a side elevational view of ball joint 350.

Central channel 341 through sleeve 340 is tapered at both ends (as shown) to allow a cable to pass through it smoothly and easily (and to improve rigidity in the arm's rigid state). The wall of channel 341 defines a socket surface at each end of channel 341, with each socket surface having a jagged profile comprising circular shoulders 342 and 343 and indentations 344 (shown in phantom view in FIG. 36). At each end of channel 341, shoulders 342 and 343 and the edges of indentations 344 are designed to bite into a convex ball surface of an adjacent ball joint 350, thus increasing friction between the convex ball surface and the sleeve 340 in contact therewith, to assist with locking the arm when the sleeves and ball joints are tightened together.

Central channel 351 through ball joint 350 is tapered at both ends (as shown) to allow a cable to pass through it smoothly and easily (and to improve rigidity in the arm's rigid state). Ball joint 350 has an annular flange 352 around its periphery, for limiting the freedom of an adjacent sleeve 340 to slide over the outer surface of ball joint 350. Ball joints 350 and sleeves 340 are shaped so as to fit together as shown in FIG. 38, with a cable (not shown) extending through their aligned central channels 341 and 351. In some implementations of FIG. 38, each ball joint is made from a hard plastic having a first hardness and each sleeve is made from a hard plastic having a second hardness (different from the first hardness) so that the harder material wedges into the softer material. For example, the ball joints can be molded from polycarbonate plastic and the sleeves from Ultem plastic (or the sleeves can be molded from polycarbonate plastic and the ball joints from Ultem plastic).

In general, the ball joints (or ball joints and sleeves) used in the locking arm employed in some embodiments of the invention preferably satisfy the following criteria: their geometry results in improved mechanical advantage to achieve greater and more reliable rigidity when tightened together; they allow arm flexibility when loosened relative to each other; they have low profile; they remove compliance in the arm when tightened together; and there is increased friction between the abutting ball and socket surfaces when they are tightened together.

Figure 39:
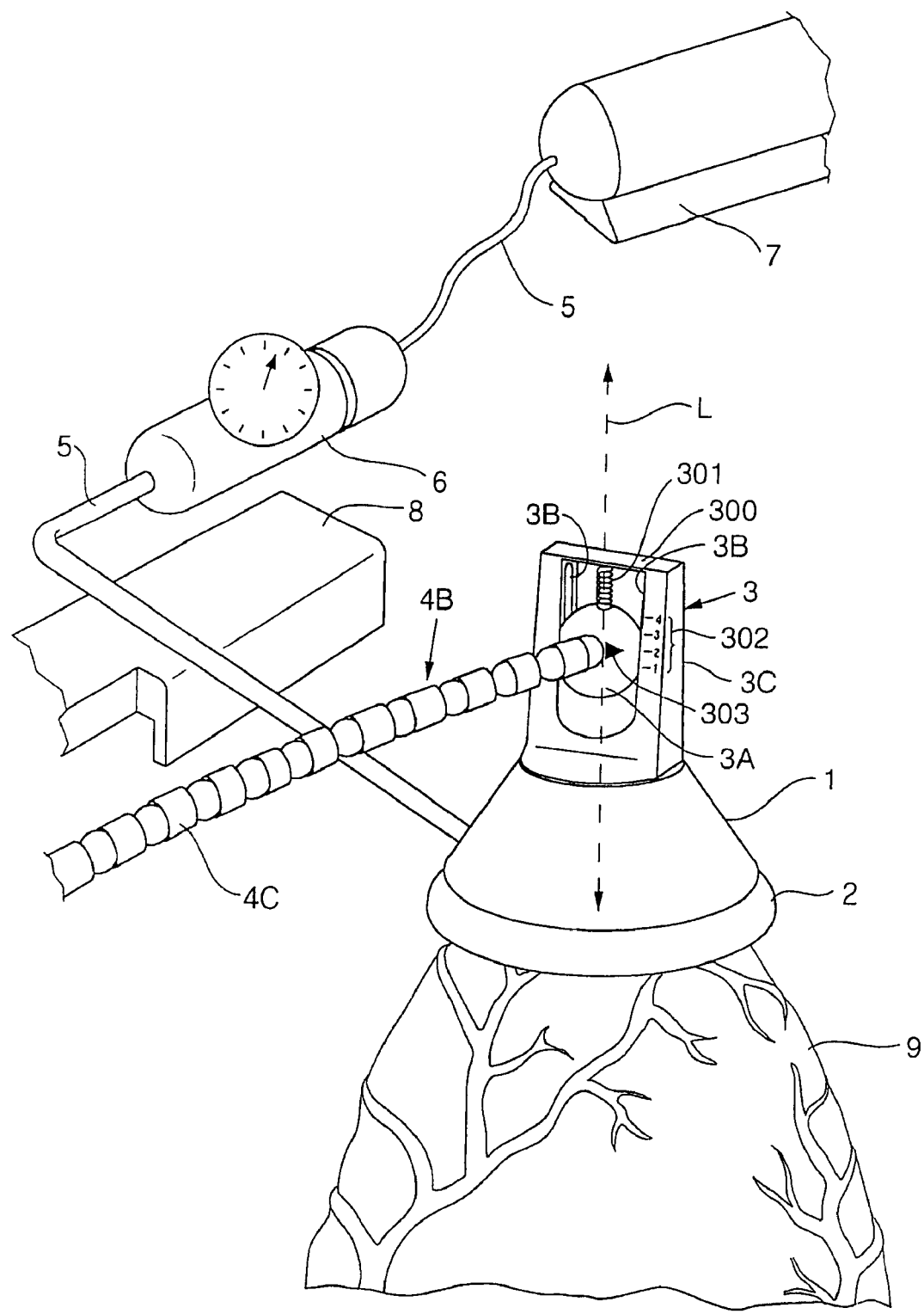
FIG. 39 is a perspective view of a portion of a variation on the FIG. 1 apparatus.

A variation on the FIG. 1 apparatus (which includes a built-in force gauge) will next be described with reference to FIG. 39. All elements of this alternative embodiment that correspond to elements of the FIG. 1 apparatus are identically numbered in FIGS. 1 and 39, and the description thereof will not be repeated with reference to FIG. 39. In the FIG. 39 embodiment, ball sliding joint 3 includes (in addition to ball 3A and U-shaped element 3C): spring support 300 (connected between the upper ends of element 3C), and spring 301 connected between support 300 and ball 3A. Element 3C is marked with a scale 302 which is oriented parallel to one of grooves 3B, and ball 3A is marked with a position indicator 303. As element 3C moves relative to ball 3A (with ball 3A riding in grooves 3B), spring 301 compresses or elongates (and thus the spring force exerted by spring 301 on support 300 and element 3C changes), and indicator 303 becomes aligned with different ones of the force index marks comprising scale 302. The relative position of indicator 303 and scale 302 provides a visual indication of the spring force being exerted at any instant by spring 301 on support 300 (and hence on element 3C). Thus, elements 300, 301, 302, and 303 implement a spring force gauge. The force gauge can be used by the surgeon to help the surgeon configure the apparatus so that it exerts safe lifting forces on the heart during use.

Figure 27:
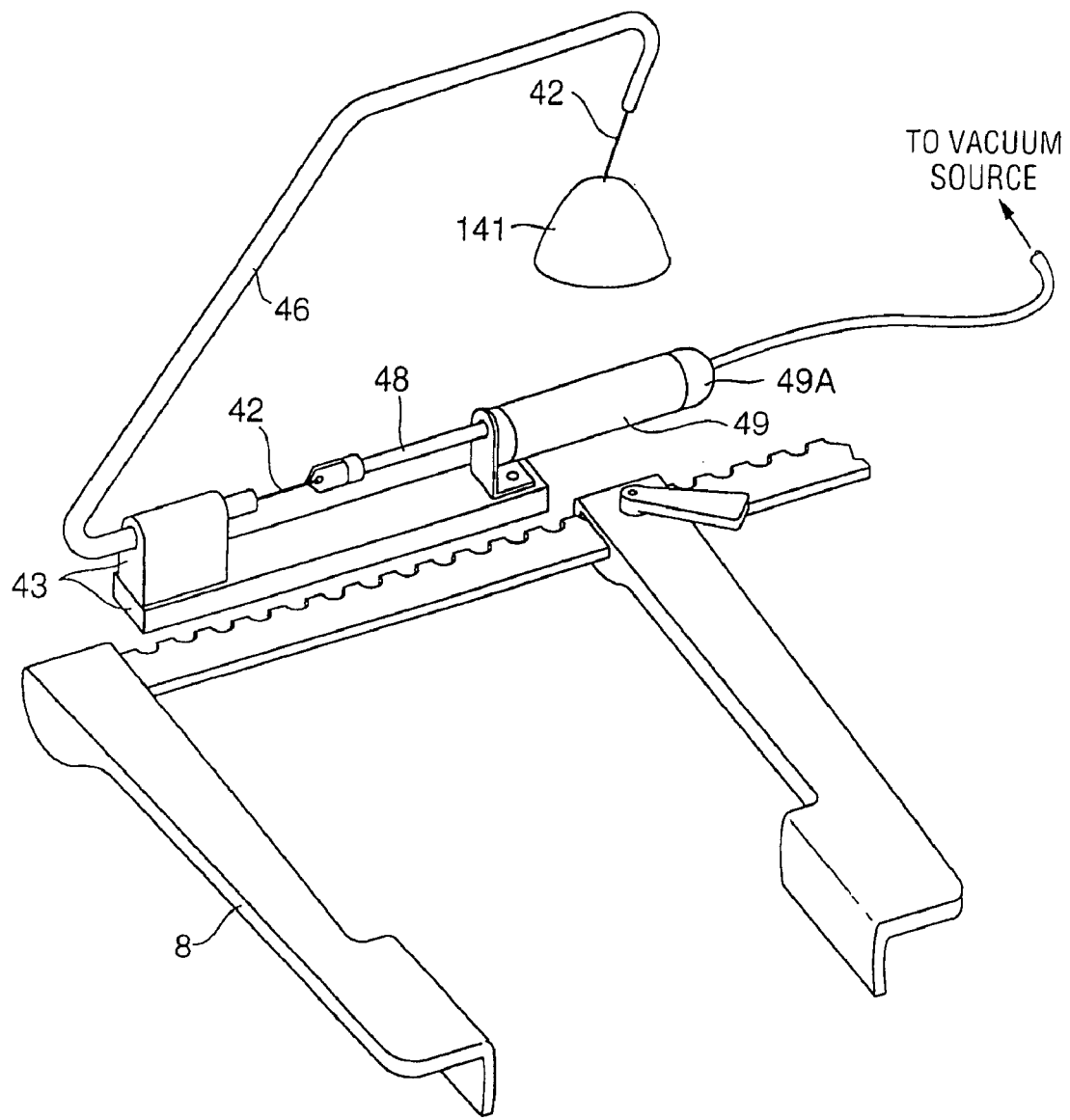
FIG. 27 is a perspective view of a portion of an alternative embodiment of the inventive organ manipulation apparatus.

Still other alternative embodiments of the invention include a bio-absorbable disc with an adhesive surface to be adhered to the heart (or other organ) surface (instead of a suction cup). The disc is releasably mounted on a compliant joint which is in turn supported by a fixed structure, so that the disc does not constrain normal beating motion of the heart (or normal motion of the other organ) during gross movement of the disc and organ into the desired position and surgery on the organ suspended vertically below the disc in the desired position). The disc is released from the compliant joint after the surgical procedure. This can be a variation on any of the embodiments described herein with the bio-absorbable disc replacing the suction cup. For example, the FIG. 27 embodiment includes bio-absorbable disc 141 (having an adhesive, concave lower surface) in place of cup 41 (and suction line 45) of FIG. 7. The FIG. 27 embodiment is otherwise identical to the above-described FIG. 7 embodiment, and the description of its components which are identically numbered in FIGS. 7 and 27 will not be repeated.

Use of a suction cup in accordance with the invention desirably supports the blood flow structures of the heart (or other organ) being manipulated to prevent them from collapsing under externally applied forces (for example, to compensate for compression during stabilization to permit surgery).

The suction cup of the inventive apparatus can be preformed of hard material (such as hard plastic) or flexible material (such as silicon rubber), with its inner surface lined with biocompatible foam or ocher materials currently used in neuro-sponges (to absorb blood and other bodily fluid, thereby improving the cup's grip on the heart or other organ). To preform the cup in a desirable shape (a shape likely to conform with the organ which it will manipulate), a rubber cast of a typical organ surface can be made and the cast can then be used to manufacture (e.g., mass produce) the cup, or a typical organ surface can be scanned with a laser to generate a computer model and the model can then be used to manufacture the cup.

We contemplate using an auxiliary suction member (with any of the above-described embodiments of the inventive apparatus which include a suction member and a compliant joint) under some circumstances (such as to perform certain types of heart surgery). For example, when the inventive suction member (with compliant joint) retracts a beating heart by applying suction to the apex of the heart, and the heart is suspended (by suction) below it, an auxiliary suction cup (or other suction member) can be affixed to the side of the heart to assist with rolling or moving the heart. The auxiliary suction member could be mounted to a hand-held rigid pole, or to an arm mounted to a fixed structure. The auxiliary suction member would typically have less curvature (it would be flatter) than any of the above-described suction cups which are especially designed to grip the apex of the heart. The auxiliary suction member would desirably be mounted to a compliant joint (of any of the above-described types), so that it does not compromise hemodynamic function of the organ being retracted.

The invention can be employed to manipulate (and support in a retracted position) an organ other than a beating heart. For example, it can be used to manipulate (and support in a retracted position) a liver (e.g., during a cholecystectomy) or a stomach (e.g., during a Nissen fundoplication).

The foregoing is merely illustrative and explanatory of preferred embodiments of the inventive methods and apparatus. Various changes in the component sizes and shapes, and other details of the embodiments described herein may be within the scope of the appended claims.

What is claimed is:

1. An organ manipulation apparatus, including:
    at least one suction member having an inner surface and an outer surface, wherein the suction member is configured to exert sufficient suction force on an organ to move the organ when the suction member is placed against the organ, a pressure differential is established between the inner surface and the outer surface, and the suction member is moved;
    a support structure; and
    a joint coupled between the suction member and the support structure, wherein the support structure, in a rigid configuration, and the joint are configured to support the suction member, with the organ supported by the suction member, such that the joint allows the suction member freedom to move relative to the support structure, to allow movements of the organ, while the support structure remains relatively fixed.

2. The apparatus of claim 1, wherein the support structure comprises an arm that is convertible from a flexible state to a rigid state, and from a rigid state to a flexible state.

3. The apparatus of claim 2, wherein said support arm includes a cable running through a series of ball joints, and an actuator at a proximal end portion of said support arm configured to tension said cable to transform said arm from said flexible state to said rigid state; and wherein said actuator is further configured to release tension in said cable to transform said arm from said rigid state to said flexible state.

4. The apparatus of claim 2, wherein said support arm includes a cable running through a series of alternating ball joints and sleeves, and an actuator at a proximal end portion of said support arm configured to tension said cable to transform said arm from said flexible state to said rigid state; and wherein said actuator is further configured to release tension in said cable to transform said arm from said rigid state to said flexible state.

5. The apparatus of claim 1, wherein the support structure comprises a rigid arm.

6. The apparatus of claim 1, wherein said suction member comprises a plurality of suction members.

7. The apparatus of claim 1, wherein said joint allows at least one of: freedom to rotate about a longitudinal axis of the suction member relative to said support structure when said support structure is rigid, freedom to swing relative to said support structure when said support structure is rigid, or at least limited freedom to translate along said longitudinal axis relative to said support structure when said support structure is rigid.

8. The apparatus of claim 1, further comprising a locking mechanism, wherein when said locking mechanism is in a locked configuration, said freedom of said suction member to move relative to the support structure is at least partially restricted.

9. A method for compliant retraction of an organ, said method comprising:
   retracting the organ by contacting at least one suction member to the organ and applying suction to establish a pressure differential between an inner surface and an outer surface of at least one of said at least one suction member, thereby engaging the organ, and moving the at least one suction member; and
   providing a support structure in a fixed orientation, and a joint interconnecting the at least one suction member with the support structure;
   wherein the joint permits the at least one suction member to move relative to the fixed orientation support structure in response to movement of the retracted organ.

10. The method of claim 9, wherein the support structure is in a flexible orientation when said at least one suction member is contacted to the organ, said method further including transforming the support structure from the flexible orientation to the a rigid orientation to place said support structure in the fixed orientation.

11. The method of claim 9, wherein said joint allows at least one of: freedom to rotate about a longitudinal axis of the suction member relative to said support structure when said support structure is fixed, freedom to swing relative to said support structure when said support structure is fixed, or at least limited freedom to translate along said longitudinal axis relative to said support structure when said support structure is fixed.

* * * * *

UNITED STATES PATENT AND TRADEMARK OFFICE
CERTIFICATE OF CORRECTION

| | | |
|---|---|---|
| PATENT NO. | : 8,092,369 B2 | Page 1 of 1 |
| APPLICATION NO. | : 12/837391 | |
| DATED | : January 10, 2012 | |
| INVENTOR(S) | : Peng et al. | |

It is certified that error appears in the above-identified patent and that said Letters Patent is hereby corrected as shown below:

Column 4, line 59, please delete "crates" and insert --creates--;
Column 8, line 9, please delete "element)." and insert --element.--;
Column 9, line 57, please delete "(Locking" and insert --locking--;
Column 11, line 67, please delete "long," and insert --long--;
Column 24, line 11, please delete "bail" and insert --ball--; and
Column 26, line 9, please delete "ocher" and insert --other--.

Signed and Sealed this
Sixth Day of November, 2012

David J. Kappos
*Director of the United States Patent and Trademark Office*